United States Patent
Franklin et al.

(10) Patent No.: US 6,872,384 B1
(45) Date of Patent: Mar. 29, 2005

(54) TREATMENT OF TRAUMA

(75) Inventors: Richard Franklin, London (GB); Didier S P Cowling, Langnau am Albis (CH); Jeffrey A. Hubbell, Zumiken (CH); Petra van de Wetering, Zürich (NL)

(73) Assignee: Life Medical Sciences, Inc., Little Silver, NJ (US)

( * ) Notice: Subject to any disclaimer, the term of this patent is extended or adjusted under 35 U.S.C. 154(b) by 169 days.

(21) Appl. No.: 09/644,022

(22) Filed: Aug. 23, 2000

Related U.S. Application Data

(63) Continuation-in-part of application No. 09/256,484, filed on Feb. 23, 1999.
(60) Provisional application No. 60/085,456, filed on May 14, 1998, and provisional application No. 60/073,234, filed on Feb. 23, 1998.

(51) Int. Cl.[7] .................... A61K 31/74; A61K 31/78
(52) U.S. Cl. ................. 424/78.18; 424/78.31; 424/487
(58) Field of Search .................. 424/78.18, 78.31, 424/487

(56) References Cited

U.S. PATENT DOCUMENTS

| | | | |
|---|---|---|---|
| 4,596,858 A | 6/1986 | Gregor et al. | 525/328.2 |
| 4,666,983 A | 5/1987 | Tsubakimoto et al. | 525/119 |
| 5,078,994 A | 1/1992 | Nair et al. | 424/501 |
| 5,080,893 A | 1/1992 | Goldberg et al. | 514/57 |
| 5,126,409 A | 6/1992 | Jerman et al. | 525/329.9 |
| 5,140,016 A | 8/1992 | Goldberg et al. | 514/57 |
| 5,154,706 A | 10/1992 | Cartmell et al. | 604/307 |
| 5,160,328 A | 11/1992 | Cartmell et al. | 604/307 |
| 5,204,110 A | 4/1993 | Cartmell et al. | 424/443 |
| 5,229,466 A | 7/1993 | Brehm et al. | 525/329.9 |
| 5,306,504 A | 4/1994 | Lorenz | 424/449 |
| 5,350,573 A | 9/1994 | Goldberg et al. | 424/78.06 |
| 5,385,983 A | 1/1995 | Graham | 525/330.1 |
| 5,397,567 A | 3/1995 | Lobering et al. | 424/78.04 |
| 5,423,736 A | 6/1995 | Cartmell et al. | 602/42 |
| 5,455,027 A | 10/1995 | Zalipsky et al. | 424/78.17 |
| 5,665,477 A | 9/1997 | Meathrel et al. | 428/500 |
| 5,677,276 A | 10/1997 | Dickerson et al. | 514/8 |
| 5,705,177 A | 1/1998 | Roufa et al. | 424/422 |
| 5,705,178 A | 1/1998 | Roufa et al. | 424/422 |
| 5,779,696 A | 7/1998 | Berry et al. | 606/16 |
| 5,885,566 A | 3/1999 | Goldberg | 424/78.18 |
| 5,906,997 A | 5/1999 | Schwartz et al. | 514/781 |
| 5,912,228 A | 6/1999 | Lambert, Jr. | 514/12 |
| 5,939,208 A | 8/1999 | Stoy | 428/500 |
| 5,942,487 A | 8/1999 | Ogawa et al. | 514/2 |
| 5,994,325 A | 11/1999 | Roufa et al. | 514/59 |
| 6,010,692 A | 1/2000 | Goldberg et al. | 424/78.06 |
| 6,017,301 A | 1/2000 | Schwartz et al. | 547/781 |
| 6,034,140 A | 3/2000 | Schwartz et al. | 514/781 |
| 6,039,940 A | 3/2000 | Perrault et al. | 424/78.06 |
| 6,083,930 A | 7/2000 | Roufa et al. | 514/54 |
| 6,086,863 A | 7/2000 | Ritter et al. | 424/78.06 |
| 6,127,348 A | 10/2000 | Roufa et al. | 514/59 |
| 6,133,325 A | 10/2000 | Schwartz et al. | 514/781 |
| 6,417,173 B1 | 7/2002 | Roufa et al. | 514/54 |
| 2002/0010150 A1 | 1/2002 | Cortese et al. | 514/54 |

FOREIGN PATENT DOCUMENTS

| | | |
|---|---|---|
| EP | 0068509 B1 | 8/1985 |
| EP | 0426422 A2 | 10/1990 |
| EP | 0604101 A1 | 12/1993 |
| EP | 0952171 A2 | 10/1999 |
| GB | 2215335 A * | 9/1989 |
| WO | WO 95/15352 | 6/1995 |
| WO | WO 96/24371 * | 8/1996 |
| WO | WO 97/05185 | 2/1997 |
| WO | WO 98/26789 | 6/1998 |
| WO | WO 99/38472 | 8/1999 |
| WO | WO 99/44557 | 9/1999 |
| WO | WO 99/47129 | 9/1999 |
| WO | WO 00/44808 | 8/2000 |
| WO | WO01/82863 A2 | 11/2001 |
| WO | WO01/82937 A1 | 11/2001 |

OTHER PUBLICATIONS

Hubbell, "Hydrogel systems for barriers and local drug delivery in the control of wound healing," J. Controlled Release 39 (1996) 305–313.*
Noveon, Inc. Bulletin 3: Nomenclature and Chemistry, Jan. 2002.*
Noveon, Inc. Bulletin 14: Formulating Topical Properties, Jan., 2002.*
Noveon, Inc. Bulletin 16: Bioadhesion, Jan., 2002.*
Noveon, Inc. Product Specification Carbopol® 941 NF Polymer.*
Fate of Water–Soluble Polymers Administered via Different Routes, Tetsuji et al.; J of Pharm. Sci vol. 84, No. 3, Mar. 1995 p. 349–354.

* cited by examiner

*Primary Examiner*—Robert A. Wax
(74) *Attorney, Agent, or Firm*—Coleman Subol Sapone, PC; Henry D. Coleman

(57) ABSTRACT

Provided is a method of treating an area affected by a trauma, such as a corneal wound or internal trauma, comprising administering to the affected area a trauma treating effective amount of a composition comprising a polyanionic polymer.

14 Claims, No Drawings

```
                          SEQUENCE LISTING

<160> NUMBER OF SEQ ID NOS: 17

<210> SEQ ID NO 1
<211> LENGTH: 300
<212> TYPE: PRT
<213> ORGANISM: Panaeu vanameii

<400> SEQUENCE: 1

Leu Leu Leu Ala Leu Val Ala Ala Ala Ser Ala Ala Glu Trp Arg Trp
 1               5                  10                  15

Gln Phe Arg His Pro Thr Val Thr Pro Asn Pro Arg Ala Lys Asn Pro
            20                  25                  30

Phe Arg Val Thr Lys Ser Ser Pro Val Gln Pro Pro Ala Val Arg Gly
        35                  40                  45

Thr Lys Ala Val Glu Asn Cys Gly Pro Val Ala Pro Arg Asn Lys Ile
    50                  55                  60

Val Gly Gly Met Glu Val Thr Pro His Ala Tyr Pro Trp Gln Val Gly
65                  70                  75                  80

Leu Phe Ile Asp Asp Met Tyr Phe Cys Gly Gly Ser Ile Ile Ser Asp
                85                  90                  95

Glu Trp Val Leu Thr Ala Ala His Cys Met Asp Gly Ala Gly Phe Val
            100                 105                 110

Glu Val Val Met Gly Ala His Ser Ile His Asp Glu Thr Glu Ala Thr
        115                 120                 125

Gln Val Arg Ala Thr Ser Thr Asp Phe Phe Thr His Glu Asn Trp Asn
    130                 135                 140

Ser Phe Thr Leu Ser Asn Asp Leu Ala Leu Ile Lys Met Pro Ala Pro
145                 150                 155                 160

Ile Glu Phe Asn Asp Val Ile Gln Pro Val Cys Leu Pro Thr Tyr Thr
                165                 170                 175

Asp Ala Ser Asp Asp Phe Val Gly Glu Ser Val Thr Leu Thr Gly Trp
            180                 185                 190

Gly Lys Pro Ser Asp Ser Ala Phe Gly Ile Ala Glu Gln Leu Arg Glu
        195                 200                 205

Val Asp Val Thr Thr Ile Thr Thr Ala Asp Cys Gln Ala Tyr Tyr Gly
    210                 215                 220

Ile Val Thr Asp Lys Ile Leu Cys Ile Asp Ser Glu Gly Gly His Gly
225                 230                 235                 240

Ser Cys Asn Gly Asp Ser Gly Gly Pro Met Asn Tyr Val Thr Gly Gly
                245                 250                 255

Val Thr Gln Thr Arg Gly Ile Thr Ser Phe Gly Ser Ser Thr Gly Cys
            260                 265                 270

Glu Thr Gly Tyr Pro Asp Gly Tyr Thr Arg Val Thr Ser Tyr Leu Asp
        275                 280                 285

Trp Ile Glu Ser Asn Thr Gly Ile Ala Ile Asp Pro
    290                 295                 300

<210> SEQ ID NO 2
<211> LENGTH: 25
<212> TYPE: PRT
```

-continued

```
<213> ORGANISM: Panaeus vanameii

<400> SEQUENCE: 2

Ile Val Gly Gly Val Glu Ala Thr Pro His Ser Trp Pro His Gln Ala
 1               5                  10                  15

Ala Leu Phe Ile Asp Asp Met Tyr Phe
            20                  25

<210> SEQ ID NO 3
<211> LENGTH: 20
<212> TYPE: PRT
<213> ORGANISM: Panaeus vanameii
<220> FEATURE:
<221> NAME/KEY: VARIANT
<222> LOCATION: (1)...(20)
<223> OTHER INFORMATION: Xaa = Any Amino Acid

<400> SEQUENCE: 3

Ile Val Gly Gly Val Glu Ala Thr Pro His Ser Xaa Pro His Gln Ala
 1               5                  10                  15

Ala Leu Phe Ile
            20

<210> SEQ ID NO 4
<211> LENGTH: 25
<212> TYPE: PRT
<213> ORGANISM: Panaeus monodon tryptic

<400> SEQUENCE: 4

Ile Val Gly Gly Thr Ala Val Thr Pro Gly Glu Phe Pro Tyr Gln Leu
 1               5                  10                  15

Ser Phe Gln Asp Ser Ile Glu Gly Val
            20                  25

<210> SEQ ID NO 5
<211> LENGTH: 25
<212> TYPE: PRT
<213> ORGANISM: Panaeus monodon chymotryptic

<400> SEQUENCE: 5

Ile Val Gly Gly Val Glu Ala Val Pro Gly Val Trp Pro Tyr Gln Ala
 1               5                  10                  15

Ala Leu Phe Ile Ile Asp Met Tyr Phe
            20                  25

<210> SEQ ID NO 6
<211> LENGTH: 25
<212> TYPE: PRT
<213> ORGANISM: Panaeus monodon chymotryptic

<400> SEQUENCE: 6

Ile Val Gly Gly Val Glu Ala Val Pro His Ser Trp Pro Tyr Gln Ala
 1               5                  10                  15

Ala Leu Phe Ile Ile Asp Met Tyr Phe
            20                  25

<210> SEQ ID NO 7
<211> LENGTH: 25
<212> TYPE: PRT
<213> ORGANISM: Uca pugilator enzyme

<400> SEQUENCE: 7

Ile Val Gly Gly Val Glu Ala Val Pro Asn Ser Trp Pro His Gln Ala
```

```
                1               5                   10                  15
Ala Leu Phe Ile Asp Asp Met Tyr Phe
                20                  25

<210> SEQ ID NO 8
<211> LENGTH: 20
<212> TYPE: PRT
<213> ORGANISM: Uca pugilator enzyme

<400> SEQUENCE: 8

Ile Val Gly Gly Gln Asp Ala Thr Pro Gly Gln Phe Pro Tyr Gln Leu
1               5                   10                  15

Ser Phe Gln Asp
                20

<210> SEQ ID NO 9
<211> LENGTH: 20
<212> TYPE: PRT
<213> ORGANISM: Kamchatka crab
<220> FEATURE:
<221> NAME/KEY: VARIANT
<222> LOCATION: (1)...(20)
<223> OTHER INFORMATION: Xaa = Any Amino Acid

<400> SEQUENCE: 9

Ile Val Gly Gly Gln Glu Ala Ser Pro Gly Ser Trp Pro Xaa Gln Val
1               5                   10                  15

Gly Leu Phe Phe
                20

<210> SEQ ID NO 10
<211> LENGTH: 20
<212> TYPE: PRT
<213> ORGANISM: Kamchatka crab

<400> SEQUENCE: 10

Ile Val Gly Gly Thr Glu Val Thr Pro Gly Glu Ile Pro Tyr Gln Leu
1               5                   10                  15

Ser Leu Gln Asp
                20

<210> SEQ ID NO 11
<211> LENGTH: 20
<212> TYPE: PRT
<213> ORGANISM: Kamchatka crab

<400> SEQUENCE: 11

Ile Val Gly Gly Thr Glu Val Thr Pro Gly Glu Ile Pro Tyr Gln Leu
1               5                   10                  15

Ser Phe Gln Asp
                20

<210> SEQ ID NO 12
<211> LENGTH: 20
<212> TYPE: PRT
<213> ORGANISM: Kamchatka crab
<220> FEATURE:
<221> NAME/KEY: VARIANT
<222> LOCATION: (1)...(20)
<223> OTHER INFORMATION: Xaa = Any Amino Acid

<400> SEQUENCE: 12

Ile Val Gly Gly Ser Glu Ala Thr Ser Gly Gln Phe Pro Tyr Gln Xaa
1               5                   10                  15
```

-continued

Ser Phe Gln Asp
            20

<210> SEQ ID NO 13
<211> LENGTH: 20
<212> TYPE: PRT
<213> ORGANISM: Crayfish protease

<400> SEQUENCE: 13

Ile Val Gly Gly Thr Asp Ala Thr Leu Gly Glu Phe Pro Tyr Gln Leu
1               5                   10                  15

Ser Phe Gln Asn
            20

<210> SEQ ID NO 14
<211> LENGTH: 25
<212> TYPE: PRT
<213> ORGANISM: Salmon enzyme

<400> SEQUENCE: 14

Ile Val Gly Gly Tyr Glu Cys Lys Ala Tyr Ser Gln Ala Tyr Gln Val
1               5                   10                  15

Ser Leu Asn Ser Gly Tyr His Tyr Cys
            20                  25

<210> SEQ ID NO 15
<211> LENGTH: 25
<212> TYPE: PRT
<213> ORGANISM: Atlantic cod

<400> SEQUENCE: 15

Ile Val Gly Gly Tyr Glu Cys Thr Lys His Ser Gln Ala His Gln Val
1               5                   10                  15

Ser Leu Asn Ser Gly Tyr His Tyr Cys
            20                  25

<210> SEQ ID NO 16
<211> LENGTH: 25
<212> TYPE: PRT
<213> ORGANISM: Atlantic cod

<400> SEQUENCE: 16

Ile Val Gly Gly Tyr Glu Cys Thr Arg His Ser Gln Ala His Gln Val
1               5                   10                  15

Ser Leu Asn Ser Gly Tyr His Tyr Cys
            20                  25

<210> SEQ ID NO 17
<211> LENGTH: 37
<212> TYPE: PRT
<213> ORGANISM: Atlantic cod

<400> SEQUENCE: 17

Ile Val Gly Gly Tyr Gln Cys Glu Ala His Ser Gln Ala His Gln Val
1               5                   10                  15

Ser Leu Asn Ser Gly Tyr His Tyr Cys Gly Gly Ser Leu Ile Asn Trp
            20                  25                  30

Val Val Ser Ala Ala
            35

TREATMENT OF TRAUMA

This application is a continuation-in-part of U.S. Ser. No. 09/256,484, filed Feb. 23, 1999 which claims benefit of 60/073,234 filed Feb. 23, 1998 and claims benefit of 60/085,456 filed May 14, 1998.

The invention relates to the use of a polyanionic polymer that can be a microgel, with or without certain enzymes, for treating wounds, such as corneal ulcerations, internal trauma, such as that caused by surgery; as well as for treating inflammatory diseases and their sequelae, and to reducing adhesions or inhibiting adhesion formation. The invention further relates to the use of an enzyme in any pharmaceutically acceptable carrier for the treatment of inflammatory diseases, corneal wounds and inhibiting adhesion formation.

Various treatments for tissue trauma or wounds are known in the art. However, particularly with regard to corneal ulcerations or abrasions, for example, there are few, if any, non-invasive procedures that effectively and economically reduce or prevent permanent damage to the cornea. Accordingly, a not uncommon result of such injuries to the cornea is partial or total blindness in the affected eye. New non-invasive treatments would be welcome.

The formation of adhesions on internal organs and tissues, such as between the body wall and internal organs, following internal surgery or infection, is a significant medical problem. New methods and treatments for treating internal trauma and inflammatory diseases to suppress adhesion formation are needed.

Other wounds for which improved treatments have been obtained include cutaneous wounds such as decubitus ulcers, venous ulcers, burns, or pressure sores.

Occasionally, normally beneficent inflammatory responses go awry and the agents of the inflammatory processes turn against otherwise healthy autologous tissue. Autoimmune disorders, for example rheumatoid arthritis, exemplify this phenomenon. A similar phenomenon can occur in the case of prolonged localized chronic inflammation, such as that which occurs in chronic osteoarthritis. The method of the invention is particularly useful in treating or managing conditions having an associated inflammatory process in which the detrimental effects of an inflammatory response predominate over the beneficial effects.

SUMMARY OF THE INVENTION

The invention relates, among other things, to a method of treating an area affected by a trauma, including trauma from corneal wounds and internal trauma that includes administering to the affected area a trauma treating effective amount of a composition comprising a polyanionic polymer or an enzyme such as a protease or both. In some embodiments, a non-addition polyanionic polymer, as defined in the specification below, or a microgel, is used. In some embodiments, a pre-formed polymer is preferred. A polyanionic polymer having hydrolytically susceptible bonds can be used. A corneal wound treated by a method of the invention can include a corneal ulcer, a corneal abrasion, or a chemical or physical insult to the cornea susceptible to giving rise to a corneal ulcer. Infected corneal ulcer are usefully treated with the methods of the invention. Internal trauma such as surgical wounds or trauma to a membrane that covers either an internal organ or tissue or the cavity in which one or more internal organs or tissues reside can be treated by a method of the invention. A membrane can be a serous membrane such as the peritoneum, the pericardium, the epicardium, and the pleura. A membrane can also be an epithelium, including the endothelium or a meninges. The treated internal trauma can include trauma to a tendon or a tendon sheath or to a nerve or a nerve sheath, or an internal surgical wound. The internal trauma can be one susceptible of giving rise to adhesions and the amount of polyanionic polymer administered is an amount effective to inhibit or reduce formation or reformation of adhesions.

The invention can relate to a method for reducing or inhibiting the formation or reformation of adhesions comprising the step of administering to an area affected by a trauma susceptible to giving rise to adhesions an effective amount of a composition comprising a polyanionic polymer, such as a non-addition polyanionic polymer or a polymer forming a microgel, and more preferably a pre-formed non-addition polyanionic polymer. The invention can also relate to a method of inhibiting or reducing the formation of adhesions following implantation of an implantable device.

In some embodiments of the invention, a method of treating an inflammatory disease is provided, which can include administering to an area affected by the disease, an inflammatory disease treating effective amount of a composition comprising one or more of the following: a polyanionic polymer or a protease that has an activity comprising at least two of a chymotrypsin, trypsin, collagenase, and elastase activity. In other embodiments, the invention provides a method of treating a corneal wound that can include administering to an affected area an effective amount of a composition comprising a protease that has an activity comprising at least two of a chymotrypsin, trypsin, collagenase, and elastase activity. Examples of an inflammatory disease can include osteoarthritus, rheumatoid arthritis, cervical spondylosis, cumulative trauma disorder (harmful and painful condition caused by overuse or overexertion of some part of the musculoskeletal system, often resulting from work-related physical activities; it is characterized by inflammation, pain, or dysfunction of the involved joints, bones, ligaments, and nerves), endometriosis, pelvic inflammatory disease, adhesive peritonitis, appendicitis, peridentitis, pericarditis or pleuritis. Examples of cumulative trauma disorder can include tendonitis, tenosynovitis or carpal tunnel syndrome. In some embodiments, the inflammatory disease is susceptible of giving rise to adhesions and the inflammatory disease treating effective amount is effective to inhibit or reduce the formation of such adhesions.

Methods of the invention can include the administration of one or more of the following: a steroid, a nonsteroidal anti-inflammatory agent; a streptokinase, a fibrinolytic agent, a multifunctional hydrolase having an activity comprising at least two of a chymotrypsin, trypsin, collagenase or elastase activity, an antagonist of an inflammatory cytokine or a surfactant.

In some embodiments, the invention provides compositions that can include a protease or a hydrolase. The protease or hydrolase can have an activity comprising at least two of a chymotrypsin, trypsin, collagenase, and elastase activity. The protease or hydrolase can be a multifunctional enzyme that is (a) a first enzyme and has at least about 60% sequence similarity with a reference sequence which is AA64-300 of SEQ ID NO:2 or AA1-300 of SEQ ID NO:2 or a sequence differing from these by at least one of the residue differences found in SEQ ID NO:4, 6, 8, 10, or 12 or (b) a second enzyme which is *Panaeus vanameii* 1, *Panaeus vanameii* 2, *Panaeus monodon* chymotryptic-1, *Panaeus monodon* tryptic, *Panaeus monodon* chymotryptic-2, *Uca pugilator* enzyme I, *Uca pugilator* enzyme II, Kamchatka crab IA, Kamchatka crab IIA, Kamchatka crab IIB, Kamchatka crab IIC, Crayfish protease 1, Salmon enzyme 1, Atlantic cod I, Atlantic cod II, or third Atlantic Cod trypsin.

In some embodiments, the invention provides polyanionic polymers and methods which can include administering such polyanionic polymers. For example, provided are methods of administering an effective amount of a composition comprising a non-addition polyanionic polymer (which is optionally a microgel) made from one or more ethylenically unsaturated compounds (where strands of such polymer can optionally be linked by at least one linking moiety comprising a hydrolytically susceptible bond), one or more of which can have:

i) one or more functional groups that can be titrated with base to form negatively charged functional groups, or ii) one or more precursor groups that are precursors of the functional groups that can be titrated with base; which precursor groups are converted to the functional groups;

In some embodiments, the polymer functional groups can include —C(O)OR$^4$; —O—S(O$_2$)OR$^4$, —S(O$_2$)OR$^4$; or —S(O)OR$^4$; wherein R$^4$ is hydrogen, and wherein precursor groups are selected from —C(O)OR$^4$, —OS(O$_2$)OR$^4$, —S(O$_2$)OR$^4$, or —S(O)OR$^4$; wherein R$^4$ is a cleavage permitting group, preferably independently C$_1$–C$_6$ normal or branched alkyl, phenyl, or benzyl.

In some embodiments, iii) the mole fraction of total ethylenic double bonds in the combination from which the crosslinked polyanionic polymer can be made that is contributed by the ethylenically unsaturated crosslinking agent is 0.02 or less, or preferably 0.01 or less in some embodiments.

In some embodiments, the polyanionic polymer is a microgel (meaning, typically, that it is appropriately crosslinked).

In some embodiments, iv) the ratio of macroviscosity of the polyanionic polymer composition to the microviscosity of the polyanionic polymer composition is 10,000 or less. In some embodiments, the polymer is pre-formed. In some embodiments, the polymer can be a non-addition polymer, as defined in the specification below.

In some embodiments, polymers of the invention can be made from one or more ethylenically unsaturated compounds can be represented by the structure:

(I)

wherein:

Y is —C(O)OR$^4$; —O—S(O$_2$)OR$^4$; —S(O$_2$)OR$^4$; or —S(O)OR$^4$; wherein R$^4$ is hydrogen or a cleavage permitting group, preferably, C$_1$ to C$_6$ normal or branched alkyl, phenyl, or benzyl;

X is a direct bond; a straight or branched alkylene group having two to six carbon atoms, one or more of which can be replaced by O, S, or N heteroatoms, provided that there is no heteroatom in a position α or β to Y; phenylene; a five or six membered heteroarylene having up to three heteroatoms independently selected from O, S, and N, provided that neither Y or R$^3$R$^2$C=C(R$^1$)— is bonded to a heteroatom (phenylene, oxazolylene, isoxazolylene, pyridazinylene, pyrimidinylene are ro examples of preferred arylenes); and R$^1$, R$^2$, and R$^3$ are independently selected from, hydrogen, C$_1$–C$_6$ alkyl (or C$_1$–C$_4$ or C$_1$–C$_3$ alkyl), carboxy, halogen, cyano, isocyanato, C$_1$–C$_6$ hydroxyalkyl (or C$_1$–C$_4$ hydroxyalkyl), alkoxyalkyl having 2 to 12 (or 2 to 6) carbon atoms, C$_1$–C$_6$ haloalkyl (or C$_1$–C$_4$), C$_1$–C$_6$ cyanoalkyl (or C$_1$–C$_4$), C$_3$–C$_6$ cycloalkyl, C$_1$–C$_6$ carboxyalkyl (or C$_1$–C$_4$ carboxyalkyl), aryl, hydroxyaryl, haloaryl, cyanoaryl, C$_1$–C$_6$ alkoxyaryl (or C$_1$–C$_4$ alkoxyaryl), carboxyaryl, nitroaryl, or a group —X—Y; wherein alkyl or alkoxy groups are either linear or branched and up to Q-2 carbon atoms of any C$_3$–C$_6$ cycloalkyl group, wherein Q is the total number of ring carbon atoms in the cycloalkyl group, are independently replaced with O, S, or N heteroatoms; with the proviso that neither doubly-bonded carbon atom is directly bonded to O or S; and wherein aryl is phenyl or a 5 or 6 membered heteroaryl group having up to three heteroatoms selected from the group consisting of O, S, and N. In some embodiments of the invention, R$^1$, R$^2$ and R$^3$ can be independently hydrogen or C$_1$–C$_3$ alkyl and X is a direct bond or C$_1$–C$_3$ alkylene. The cleavage permitting group can include, in some embodiments, one or more C$_1$ to C$_6$ normal or branched alkyl, phenyl or benzyl groups. In the above structure, aryl means phenyl or a 5 or 6-membered heteroaryl group having up to Q-2 heteroatoms independently selected from O, S, and N; wherein Q is the total number of atoms in the ring.

In some embodiments, the polyanionic polymer is a crosslinked polyanionic polymer. In some embodiments, the polymers are characterized by a mole fraction of ethylenic double bonds in the combination from which the polyanionic polymer is made that is contributed by the ethylenically unsaturated crosslinking agent is 0.02 or less, preferably 0.01 or less. In some embodiments of the invention, the ethylenically unsaturated crosslinking agent is an allylether of sucrose or an allyl ether of pentaerythritol. In some embodiments, the ethylenically unsaturated crosslinking agent can be, for example, an allyl ether of pentaerythritol or pentaerythritol triacrylate. In some embodiments, the unsaturated crosslinking agent is an acrylate of pentaerythritol. In some embodiments, the unsaturated crosslinking agent can be an acrylate-ester-acrylate pentaerythritol.

In some embodiments, the polyanionic polymer is crosslinked by reaction of a crosslinking agent with polyanionic polymer optionally having (or derivatized to have) one or more pendant functional groups on the polyanionic polymer capable of reacting with a functional group of the crosslinking agent.

In some embodiments, the methods of the invention can be practiced with a polyanionic polymer which has (or is functionalized to have) one or more pendant first functional groups selected from hydroxy, acyl halide, chloroformate, and mercapto; and wherein the crosslinking of the polyanionic polymer can be by reaction of a crosslinking agent having second functional groups reactive with the first functional groups. In some embodiments, the pendant first functional groups can be mercapto groups and the second functional groups can be vinylic double bonds. The crosslinking agent can be the diacrylate of an α,ω-diol, such as ethylene glycol or polyethylene glycol, or the diacrylate of a chain extended α,ω-diol, wherein the chain extensions comprise residues of a hydroxy carboxylic acid selected for example from glycolic acid, lactic acid, 3-hydroxypropionic acid, hydroxylated 3-methylbutyric acid, hydroxyvaleric acid and hydroxy proline (hydroxylated C$_1$–C$_5$ carboxylic acids and hydroxy proline). In some embodiments, the pendant first functional groups can be hydroxyl groups, the second functional groups can be carboxylic acid chloride or chloroformate groups, with the crosslinking agent comprising a residue of either an α,ω-diol or a chain extended α,ω-diol. The crosslinking agent can include, for example, a chain extended α,ω-diol (for example, ethylene glycol or polyethylene glycol) wherein the chain extensions can include residues of a hydroxy carboxylic acid such as glycolic acid, lactic acid, 3-hydroxypropionic acid, 3-methylbutyric, acid, hydroxyvaleric acid, and hydroxy proline, or residues of an amino acid such as glycine, alanine, glutamic acid, and aspartic acid. In some embodiments, the functionalized polyanionic polymer is polyacrylic acid having at least one N-(2-mercapto)ethyl carboxamide group optionally also having at least one pendant first functional group that is a mercapto group.

In some embodiments, the ethylenically unsaturated linking agent (which can be a crosslinking agent) comprises an ethylenically unsaturated derivative of a multidentate compound, comprising two or more two or more ethylenically unsaturated moieties, each such moiety being linked to the multidentate compound through a hydrolytically susceptible bond. For example, the which multidentate compound can comprise two or more functional groups that can be, independently, hydroxy, amino, or mercapto groups; wherein the derivative can include two or more ethylenically unsaturated moieties linked to a different oxy, amino, or thio group of the residue of the multidentate compound through an ester, thioester, or amide bond. The multidentate compound can be an α,ω-diol, or ethylene glycol, diethylene glycol, or polyethylene glycol. The α,ω-diol can be polyethylene glycol. The multidentate compound can be an α,ω-diamine, such as ethylene diamine. In some embodiments, the multidentate compound can be, for example, an amino aliphatic alcohol, an amino aliphatic diol, an amino aliphatic triol, a hydroxyl aliphatic diamine, and a hydroxyl aliphatic triamine an amino aliphatic thiol, an amino aliphatic dithiol, an amino aliphatic trithiol, a mercapto aliphatic diamine, or a mercapto aliphatic triamine. The hydrolytically susceptible bond can, in some embodiments, be formed of or more residues of a hydroxy carboxylic acid such as glycolic acid, lactic acid, 3-hydroxypropionic acid, 3-methylbutyric acid, hydroxyvaleric acid, or hydroxy proline. The hydrolytically susceptible bond-forming group can include, in some embodiments, at least one residue of an amino acid.

In some embodiments, the invention provides a method of isolating a multifunctional proteolytic enzyme from a biological specimen comprising extracting the multifunctional proteolytic enzyme using fresh water. In some embodiments, the biological specimen is not mechanically disrupted. Some embodiments provide for applying the fresh water extract to an affinity column having a ligand, wherein the ligand is aminophenylboronate. Some embodiments of the invention provide a method of isolating a multifunctional proteolytic enzyme from a biological extract that includes applying the biological extract to an affinity column having a ligand, wherein the ligand can be aminophenylboronate.

In some embodiments, a method is provided that includes a composition comprising a polymer, wherein the polymer comprises a polypeptide comprising residues of one or more polycarboxylic amino acids. In some embodiments, the polymer can be a dicarboxylic amino acid with the formula:

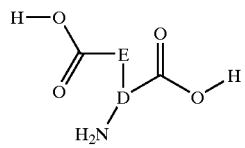

wherein;

D is a straight or branched alkylene having substituent E that is a straight or branched alkylene wherein D and E taken together have up to 10 carbon atoms. The dicarboxylic amino acid can be, for example, glutamic acid, aspartic acid, poly(glutamnic acid) or poly(aspartic acid). In some embodiments, a polyanionic polymer has a main chain comprising one or more hydrolytically susceptible selected from the group consisting of ester, carbonate, thiocarbonate, urethane, carbamate and urea. In some embodiments, one or more hydrolytically susceptible links can include a residue of a hydroxy acid. The α-hydroxy acid can be, for example, lactic acid. The main chain of the polyanionic polymer can include a residue of an α,ω-diol, diamine or dithiol.

Some embodiments involve use of a polyanionic polymer formed by the reaction of the bis-acrylate of ethylene glycol, the bis-acrylamide of ethanediamine, or N-(2-acryloyloxy) ethyl acrylamide with a bis-mercapto end-capped polyanionic oligomer and made by polymerization of one or more ethylenically unsaturated compounds.

DETAILED DESCRIPTION

For the purposes of this application, the terms listed below shall have the following respective meanings:

AM is an anionic monomer consistent with the monomers described in the Summary. Note that consistent with the Summary and the further description below, not all of the monomer contributing to a PAP is itself anionic.

MW is molecular weight.

PAA is a Poly(acrylic acid) based polymer.

PAO is polyalkylene oxide, of which PEG is an example. PAOs are typically have C2 to C4 repeating units, with C3 and C4 repeating units typically blended with C2 (ethyleneoxide) to increase water solubility. The size of the PAO segments is preferably such the molecular weights for 90% or more of the segments is 50 kd or 40 kd or less. In one embodiment, 95%, 98% or more of the segments fall within these size limits. Preferably, the average molecular weight of the segments is from 20 kd to 40 kd, or 25 kd to 35 kd. Preferably, PAO segments have molecular weight averages of at least 500, more preferably at least 1,000.

PAP is a polyanionic polymer in accordance with the polymer described in the Summary.

PEG is polyethylene glycol.

acid number refers to the amount of potassium hydroxide in milligrams needed to neutralize a gram of a dry material. A material is dry if it contains not more that 2% by weight of water, an organic solvent, or organic monomer.

aliphatic includes both aliphatic and cycloaliphatic, unless otherwise indicated.

alkyl means a linear or branched alkyl group having 1–6 carbon atoms and including halogen substitution of one or more of the hydrogens of the alkyl group.

antagonist of an inflammatory cytokine: shall include any substance that tends to nullify the action of an inflammatory cytokine, for example as a drug that binds to a cell receptor without eliciting a biological response. Inflammatory cytokines shall include any cytokine protein or biological factor capable of stimulating an inflammatory response in living tissue.

cleavage-permitting group means a moiety containing $OR^4$ in which the $OR^4$ group can be chemically altered, substituted or exchanged so that the residue is —OH or —O$^-$.

clearable polymers refers to polyanionic polymers with the meaning ascribed in Section 6 of this specification.

cumulative trauma disorder means a trauma caused by repetitive motion, repetitive stress or repetitive injury to a portion of the body. Examples of cumulative trauma disorder include, but are not limited to, tendonitis, tensynovitis or carpal tunnel syndrome.

effective amount: The meaning of "effective amount" will be recognized by clinicians but includes an amount effective to reduce, ameliorate or eliminate one or more symptoms of the disease sought to be treated or the condition sought to be avoided or treated, or to otherwise produce a clinically recognizable change in the pathology of the disease or condition.

enzymatically active segment means a segment of a multifunctional protein having activity comprising at least one of a chymotrypsin, trypsin, collagenase, elastase or exo peptidase activity.

fibrinolytic agent: Fibrinolysin or agents that convert plasminogen to fibrinolysin. They may be endogenous or exogenous like the bacterial enzymes used in thromboembolism.

hydrogel is a combination with water of a hydrophilic polymer, which may be linear, branched, covalently crosslinked, ionically crosslinked, physically crosslinked, or crosslinked by hydrogen bonding. A hydrogel has 50% or more water by weight. Examples of hydrophilic polymers that form hydrogels are carboxymethylcellulose, carboxypolymethylene, and poly(hydroxyethyl methacrylate).

hydrolase means an enzyme that degrades bonds formed by dehydration reactions such as amide, ester, or ether bonds. The term encompasses, but is not limited to, proteases such as trypsin and chymotrypsin.

hydrolytically susceptible: A hydrolytically susceptible polymer is one that contains ester, amide, carbamate or anhydride bonds, or the sulfur or nitrogen-containing analogs (such as ureylene groups, imidoesters, thioesters, and the like) positioned to allow the polymer to hydrolyze over time to smaller component polymers. Such bonds are hydrolytically susceptible bonds.

inflammatory disease means an inflammatory response which causes injury to autologous tissues. Inflammatory diseases include, but are not limited to, rheumatoid arthritis, osteoarthritis, cervical spondylosis, cumulative trauma disorder, endometriosis, pelvic inflammatory disease, adhesive peritonitis, appendicitis, pericarditis and pleuritis.

isoform means a naturally occurring sequence variant of a substantially homologous protein within the same organism. Preferably, the isoform shares at least about 80% identity, and more preferably, at least about 85% identity with a reference sequence.

krill-derived multifunctional protein means a multifunctional protein having the same sequence as a protein isolated from krill having the properties of the protein described in the section entitled "Preferred Characteristics of the Multifunctional Protein." This protein is also referred to as the "krill-derived multifunctional hydrolase" and includes all isoforms of the protein. The amino acid sequence included in SEQ ID NO:1, SEQ ID NO:2, SEQ ID NO:3, SEQ ID NO:4, SEQ ID NO:5 or SEQ ID NO:6 or other isoforms thereof or chimeric polypeptides thereof are examples of krill-derived multifunctional proteins.

labile spacer group shall include a chemical functional group which is susceptible to enzymatic or non-enzymatic hydrolysis or oxidation. The labile spacer group can, in some embodiments, have one or more residues of a hydroxy carboxylic acid such as glycolic acid, lactic acid, 3-hydroxypropionic acid, 3-methylbutyric acid, hydroxyvaleric acid, or hydroxy proline. The labile spacer group can include, in some embodiments, at least one residue of an amino acid. Optionally, the hydrolytically susceptible bonds are substituted with labile spacer groups.

linking moiety comprising a hydrolytically susceptible bond refers to a chemical moiety including at least one hydrolytically susceptible bond that links one segment of polymer to another. Such a linking moiety can join two ends of linear polymer, thereby lengthening the polymer, or provide a crosslinker. Linking moieties can be formed with linking agents or by reaction of functional groups on respective segments of polymer.

microgel means a viscoelastic mass of discrete particles, each discrete particle comprising crosslinked polyanionic polymer and each particle having a size in its aqueous swollen state at neutral pH of between 0.1 and 1000 $\mu$m. The particles of aqueous swollen polyanionic polymer have 70% or more water and the crosslinking is ionic, covalent, or through hydrogen bonding.

microviscosity is measured, for example, by any method set forth in R. Y. Lochhead et al., "Poly(acrylic acid) Thickeners: The Importance of Gel Microrheology and Evaluation of Hydrophobically Modified Derivatives as Emulsifiers," in *Polymers in Aqueous Media*, pp. 113–147, 1989, which document is incorporated by reference herein in its entirety. One such method measures microdiffusion with bimodal gold sols, for example allowing for microdiffusion to be measured for a microstructure centered around 10 nm and 100 nm.

mono or disaccharide means such a saccharide or disaccharide (such as sucrose), which can be reduced to the nonreducing form or oxidized to contain up to one carboxylic acid.

multidentate compound is a compound having two or more functional groups selected from hydroxy, amino, or mercapto (thiol). Examples of multidentate compounds include ethylene glycol, amino ethanol, polyethylene glycol, glycerol, and pentaerythritol.

multifunctional protein means a protein having activity comprising at least one of a chymotrypsin, trypsin, collagenase, elastase or exo peptidase activity or asialo $GM_1$ ceramide binding activity, and substantial homology to at least a segment of a krill-derived multifunctional protein.

neutral functional group means a functional group that is not titrated by acid or base.

Non-addition polymer is a polymer wherein the polyanionic polymer segments are not formed by the addition reaction of a strong nucleophile (excluding radicals) with an ethylenic unsaturation in a second molecule. Provided this condition is met, a non-addition polymer, for the purposes of this application, can include any polymer where such polyanionic segments are produced by any means including free-radical polymerization, cationic polymerization, or anionic polymerization, as well as polymers formed by condensation reactions. It should be understood that the linking moieties or linking agents used in, or used to form, the polymers can be formed by any appropriate chemistry—even though such moieties or agents can have polymeric components.

nonsteroidal anti-inflammatory agent: Any anti-inflammatory agent that inhibits the production of prostaglandins.

physiological pH means a pH between 6.5 and 7.5.

polyanionic polymer means a polymer having an acyclic backbone and having ionizable functional groups, for example carboxy groups, that become negatively charged functional groups, for example carboxylate anions, at physiological pH. A gram of polyanionic polymer has 0.001 moles or more of functional groups that can be titrated with KOH. The ionizable functional groups can be directly chemically bonded to the polymer backbone or they can be chemically bonded to a side group or side chain that is in turn chemically bonded to the main chain. Carboxypolymethylene is an example of a polyanionic polymer in which the ionizable functional group is directly bonded to the main chain. α-Poly(glutamic acid) is an example of a polyanionic polymer in which the ionizable functional group is bonded to a side group that is an ethylene group.

pre-formed polymer is a polymer that is chemically formed ex situ, prior to administration to a subject.

reference protein or sequence means a reference protein sequence which is AA64-300 of SEQ ID NO:1 or AA1-300 of SEQ ID NO:1 or a sequence differing from these by at least one of the residue differences tabulated below:

| Reference | Change |
|---|---|
| between $Ala^8$–$Ala^9$ | insert Thr |
| $Ala^{12}$ | Ser |
| $Lys^{30}$ | Asn |
| $Val^{35}$ | Pro |
| $Thr^{36}$ | Ser |
| $Ser^{38}$ | Val |
| $Ser^{39}$ | Ala |
| $Glu^{53}$ | Pro |
| $Pro^{57}$ | Gln |
| $Val^{58}$ | Ser |
| $Ala^{59}$ | Lys/Del |
| $Pro^{60}$ | Ser/Lys/Del |
| $Arg^{61}$ | Lys/Ser/Del |
| $Asn^{62}$ | Thr |
| $Met^{68}$ | Gln/Gly |
| $Cys^{89}$ | Phe |
| $Asp^{96}$ | Glu |
| $Glu^{97}$ | Asp |
| $Leu^{100}$ | Val |
| $Ala^{103}$ | Arg |
| $Met^{106}$ | Val |
| $Ala^{109}$ | Arg |
| $Ser^{120}$ | Lys |
| $His^{122}$ | Leu |
| $Glu^{124}$ | Asp |
| $Thr^{128}$ | Ser |
| $Gln^{129}$ | Arg |
| $Val^{130}$ | Met |
| $Arg^{131}$ | Ser |
| $Thr^{133}$ | Ile |
| $Thr^{147}$ | Leu |
| $Ser^{149}$ | Thr |
| $Glu^{162}$ | Ala |
| $Asn^{164}$ | Thr |
| $Asp^{165}$ | Pro |
| $Val^{166}$ | Glu |
| $Thr^{174}$ | Ser |
| $Ala^{178}$ | Ser |
| $Ser^{179}$ | Ala/Asp |
| $Val^{183}$ | Ile |
| $Thr^{188}$ | Val |
| $Lys^{194}$ | Arg |
| $Pro^{195}$ | Asp/Ala |
| $Ser^{198}$ | Ala |
| $Phe^{200}$ | Ser |
| $Ala^{203}$ | Ser |
| $Gln^{205}$ | Leu/Val |
| $Asp^{210}$ | His |
| $Thr^{215}$ | Ser |
| $Asp^{234}$ | Ser |
| $Gly^{237}$ | Asp |
| $Gly^{279}$ | Asn |
| $Pro^{300}$ | Ala | where Del represents a deletion.

surfactant: any surface active agent that changes the nature of a surface, including lowering the surface tension of a liquid.

substantial homology means at least about 60% sequence identity or similarity, for example 60% sequence identity.

unit of multifunctional hydrolase ("U"), as used herein with respect to the krill broad specificity serine protease and related such enzymes, is defined as the amount of enzyme that catalyzes the hydrolysis of 1 μmol of substrate per minute at 25° C., wherein succinyl-ala-ala-pro-phe-p-nitroanilide (Sigma Chemical Co., St. Louis, Mo.) is the substrate, and hydrolysis is monitored via the absorbance change at 410 nm. The extinction coefficient ε of p-nitroanilide is 8800 $M^{-1}$ $cm^{-1}$, thus the multiplication factor to convert dA/minute into U/minute of sample is 5.68, when 20 μl of sample is used.

The invention provides a method for treating wounds and other trauma to anatomical membranes of a metazoan, including but not limited to mammals, humans, food animals, such as cows, pigs, sheep, goats, and the like, companion animals, such as dogs, domestic cats, horses, and the like, and exotic animals, such as elephants, apes, large cats, whales, and the like. The term membrane is used broadly and includes tissue boundaries and tissue surfaces, such as the dura mater and the surfaces of tendons; the anterior limiting area of the cornea; membranes covering internal organs or lining the cavities in which the organs reside, which include tendons within their sheaths; and internal and external epithelia and mesothelia. The term epithelium is herein used in its broadest sense and will be understood to refer to simple, stratified, and transitional epithelia, as well as the endothelium of serous membranes. The epidermis and the conjunctival epithelium on the substantia propria of the cornea are external epithelia. Internal epithelium includes surfaces, which are sometimes denoted endothelia, such as the peritoneum, pleura, and pericardium and like membranes that cover internal structures and organs, such as the viscera, the body cavity wall, and the like.

The term trauma is intended to encompass any wound, insult, or noxious stimulus to a membrane or tissue surface. Trauma that is treated by the method of the invention may or may not result in breach of the membrane or tissue boundary. Wounds can result from a disease condition, for example vascular insufficiency or infection associated with a pathogen, burns (thermal or chemical), or from application of external force to a membrane or tissue surface by accident or surgery. Noxious stimuli includes the action of heat or corrosive chemicals, for example acids and caustics, as well as manipulation of an organ during surgery.

The term corneal wounds is intended to encompass any injury to the cornea, for example, infection by a pathogen, a corneal abrasion, a corneal ulcer, or an insult capable of giving rise to a corneal ulcer in a mammal, including but not limited to humans, food animals, such as cows, pigs, sheep, goats, and the like, companion animals, such as dogs, domestic cats, horses, and the like, and exotic animals, such as elephants, apes, large cats, whales, and the like. An insult capable of giving rise to a corneal ulcer can be chemical, for example exposure to a corrosive chemical, or it can be physical, for example impact by a foreign object or a surgical incision as in keratoplasty (e.g., corneal grafting) or keratotomy (e.g., radial keratotomy).

The method of the invention is particularly useful in the treatment of, for example, ulcerations and other injuries of corneal tissue as well as cutaneous wounds such as decubitus ulcers, venous ulcers, burns, or pressure sores. Treatment of corneal ulcers according to the method of the invention retards or arrests growth of the ulcer, which, if left unchecked, can lead to perforation. Treatment of corneal ulcers according to the method of the invention also improves the rate of healing, that is the rate of return of the cornea or skin to its pre-trauma condition, reducing the risk of opportunistic infection, and inhibits or reduces formation of scar tissue. A preferred target of the present inventive method of treatment is a corneal ulcer that is associated with an infection, such as viral infection caused by a Herpes virus (HSV), or a bacterial infection, such as one of a pseudomonad or a *Moraxella* species (as in *Moraxella bovis* that causes corneal ulcerations in cattle). In one embodiment, the present method comprises administering to an affected area of the cornea an effective amount of a composition containing a polyanionic polymer, for example a microgel from a crosslinked carboxypolymethylene. Treatment of cutaneous wounds by the present method preferably includes application to an area affected by a cutaneous wound of a polyanionic composition for which the ratio of macroviscosity to microviscosity is 10,000 or less and that, in some embodiments contains multifunctional krill-derived hydrolase. The treating practitioner will understand that area affected by a cutaneous wound varies with the size, location, and severity of the wound but includes the wound itself and an area around the wound (such as within 3 cm).

The method of the invention is likewise particularly useful in the inhibition or reduction of the incidence or severity of adhesions, for example those that frequently form between the peritoneum and viscera, or between non-adjacent areas of the peritoneum, following surgical procedures that inflict internal trauma, including internal surgical wounds. Adhesions are scar tissue that first develops as fibrous bands between two tissue surfaces that, despite being in apposition, normally have free movement relative to each other. The adhesions arise as a result of repair processes after an insult or a noxious stimulus has damaged the integrity of one or both opposing surfaces. Noxious stimuli include trauma (both surgical and accidental), infection, and any physical or chemical agent that can cause inflammation leading to a repair response. When adhesions prevent the normal movement between the affected surfaces, dysfunction of the underlying organ or pain may result. Adhesions start as thin and filmy strands, largely composed of fibrin, which are easily disrupted at this stage. With time they become organized, laying down collagen and becoming vascularized. At this stage, only surgical division will separate the adhering structures. This becomes necessary when the function of the tethered organ is impaired or viability is at risk. The method, as it relates to inhibition of post-operative formation of adhesions, is applicable to other types of adhesions apart from those of the peritoneum. For example, inhibition of formation or reformation of adhesions after adhesiolysis (removal of adhesions), tendon surgery, thoracic surgery, abdominal surgery, eye or ear surgery, spinal surgery, nerve surgery, pelvic surgery, gynecological surgery, as well as after surgery on the cranium, brain, and spinal cord.

The present method comprises treating the affected area of, in, or around a trauma; for example a surgical incision, or corneal ulcer or injury by applying to the affected area a trauma-treating effective amount of a composition that includes either a polyanionic polymer, a multifunctional hydrolase or both. The hydrolase can be a protease, particularly a multifunctional krill-derived serine protease. In a preferred embodiment, the present method comprises treating the area affected by a corneal wound or surgical wound with a composition that includes a polyanionic polymer that can contain a protease, preferably a multi-functional krill-derived protease.

The skilled artesian will recognize that the area affected by trauma of any type (the affected area) will depend on the nature, size, and location of the trauma. By way of example, in the case of a corneal wound, the affected area can be the entire exposed surface of the eye. When the trauma is an internal surgical wound involving a body cavity, the affected area includes surfaces of organs or tissues in the body cavity into which the surgical incision (wound) is made. In the case of peritoneotomy, the affected area is the entire peritoneal cavity and the organs residing within the peritoneal cavity; in the case of thoracotomy, the affected area is the entire thoracic cavity and the organs residing within the thoracic cavity. In the case of tendon surgery, the affected area includes the area of the incision and extends from 1 or 2 to as many as 15 cm from the incision of the tendon sheath and includes the surfaces of tissues surrounding the tendon and its sheath.

In one embodiment, the present method comprises treating the area affected by an internal trauma to reduce post trauma formation of adhesions by applying to the affected area an effective amount of a polyanionic polymer. The polyanionic polymer can crosslinked. Typically, the amount of polyanionic polymer in the composition is between 0.5 and 2.5 weight percent. In preferred embodiments, the composition has 1% crosslinked polyanionic polymer.

In one embodiment, the present method comprises treating the affected area of a cutaneous wound, such as a decubitus ulcer, venous ulcer, burn, or pressure sore, by applying to the affected area an effective amount of a composition comprising a polyanionic polymer that can contain a hydrolase, preferably a protease, most preferably a multifunctional krill-derived serine protease. An effective amount of a composition of this embodiment of the invention is an amount sufficient to promote debridement and to prevent odor and unwanted seepage and infection in the cutaneous wound, and preferably to cause it to heal faster that it would if it were merely cleansed and dressed.

In another embodiment, the present method comprises treating the affected area of the peritoneum, the epicardium, pericardium, or the pleura traumatized by an internal trauma by applying an effective amount of a composition comprising a polyanionic polymer that can contain a krill-derived protease, preferably a protease, more preferably a multifunctional krill-derived protease.

In yet another embodiment, the present method comprises treating the area of the spine, the meninges, for example dura mater (protective membrane for neural tissue), or nerves and nerve sheaths traumatized by surgery or injury to reduce or inhibit formation of adhesions by applying an effective amount of a composition comprising a polyanionic polymer described above that can contain a protease, preferably a krill-derived protease. Alternatively, such affected area can be treated with a hydrolase, in any pharmaceutically acceptable vehicle carrier as is known in the art.

In still another embodiment, the present method comprises treating the area of a tendon and its sheath affected by internal trauma, for example a surgical wound as in tenoplasty.

Areas subject to cumulative trauma or other trauma can be treated by administering to an area affected by the trauma, a trauma treating effective amount of a composition comprising one or more of the following: a polyanionic polymer or a protease that has an activity comprising at least two of a chymotrypsin, trypsin, collagenase, and elastase activity. Non-limiting examples of cumulative trauma disorder which can be treated by methods of the invention include tendonitis, tenosynovitis and carpal tunnel syndrome.

In another embodiment, the present method comprises treating the area affected by internal trauma to reduce formation of adhesions by applying to the affected area an effective amount of a krill-derived multifunctional protease. The krill-derived multifunctional protease can be applied to the affected area in any pharmaceutically acceptable vehicle of the known art. Pharmaceutically acceptable vehicles serve as carriers for administration of pharmacologically active material such as the multifunctional protease of the invention but do not interfere with the action of the active material or the bodily functions of the animal to which it is administered. Isotonic saline solution is an example of a pharmaceutically acceptable vehicle. Pharmaceutically acceptable vehicles can have excipients known in the art such as dextran, calcium chloride, glycine, citric acid, and sorbitol, to mention a few.

Compositions of the invention containing crosslinked polyanionic polymers can also be applied to the area affected by bowel, thoracic, cranial, tendon, and gynecological surgery to inhibit or reduce the formation or reformation of adhesions.

In yet another embodiment, the invention provides a method for treating a surgical implant with a composition comprising a polyanionic polymer, which can be a microgel, to reduce adhesion formation between the implant and areas of tissue surrounding the implant or between different areas of the tissue surrounding the implant by applying to the surface of the surgical implant a coating including the composition having a thickness from between about 0.1 mm to about 5 mm. Surgical implants with which the method can be used include joint and bone prostheses, including prosthetics of the inner ear, cranial plates, and cardiac pacemakers, drug delivery implants and in-dwelling catheters, among others.

In still another embodiment, the present method comprises treating or managing inflammatory diseases or conditions with an associated inflammatory component, such as rheumatoid arthritis or other autoimmune disorders, by administering a composition comprising a polyanionic polymer, an enzyme, preferably a hydrolase, or both. The composition can be administered, for example, to an area affected by the condition or disease with an inflammatory component or sequelae thereof. Further non-limiting examples of conditions that are included in the method of this embodiment include localized chronic inflammation, such as that which occurs in chronic osteoarthritis.

The crosslinked polyanionic polymers used in the method of the invention can be made by any method that provides a crosslinked polymer having an acyclic backbone and functional groups capable of ionizing to an anionic form under physiological conditions. For example, the polyanionic polymers used in the method of the invention can be obtained by polymerization of a mixture that includes an ethylenically unsaturated crosslinking agent and at least one monomer that has an ionizable functional group capable of becoming negatively charged. Typically, the ionizable functional group is a base-titratable functional group. The carboxy group is an example of a base titratable functional group. The polyanionic polymer can also be obtained from a precursor polymer having precursor functional groups that can be hydrolyzed to the ionizable functional groups that, in turn, can become negatively charged. For example, a carboxylate ester is a precursor for a carboxy group which, when treated with base, becomes a negatively charged carboxylate anion. The precursor polymer can be obtained by polymerization of a mixture that includes one or more monomers at least one of which has a precursor for a functional group that is capable of becoming negatively charged. The precursor group can be converted to the functional group capable of becoming negatively charged by, for example, hydrolysis, or any other means as will be obvious to one skilled in the art from inspection of the chemical structure of the precursor group. Conversion of the precursor group can be made to occur prior to, at the time of, or after administration of a composition.

The backbone, or main chain, of polyanionic polymers useful in the practice of the invention includes repeat units that can be derived from polymerization of one or more monomers of structure I, wherein the double bond shown is disposed to polymerization at least by free radical polymerization.

$$(R^3)(R^2)C\!=\!C(R^1)\!-\!X\!-\!Y \tag{I}$$

In structure I, $R^1$, $R^2$, and $R^3$; X; and Y are defined as set forth above.

Examples of suitable monomers include acrylic acid, methacrylic acid, allyl sulfonic acid, itaconic acid, maleic acid or its anhydride, itaconic acid, citraconic acid, to mention a few. Many other monomers that can be used to make polyanionic polymers that form microgels with water are described by Huang et al., U.S. Pat. No. 4,509,949, incorporated herein by reference.

In reference to crosslinked polyanionic polymers that can form microgels, the term backbone and main chain are used interchangeably and will be understood to refer to that portion of the polymer chains not derived from crosslinking agents.

In some embodiments, the microgel has a particle size between 1 and 500 µm in its aqueous swollen state at a pH between 6 and 8. In other embodiments, the microgel has a particle size between 10 and 500 µm in its aqueous swollen state at a pH between 6 and 8.

The polyanionic polymers used in the method of the invention can be homopolymers, having repeat units derived from only one monomer described by structure I, or they can be multipolymers derived from polymerization of a mixture of any number of monomers of structure I. Co-, ter-, quatra-, and other multipolymers can include repeat units from monomers that do not bear ionizable groups or precursors therefor, for example styrene, that are capable of copolymerizing with the monomers of structure I, with the proviso that the final polymer has 0.001 or more moles, preferably 0.0014 or more moles, more preferably 0.01 mole or more, of base titratable functional groups per gram of polymer (on a commercially acceptable dry basis). A base titratable functional group is a functional group, for example a carboxy group, that can be titrated with KOH.

In preferred embodiments, polyanionic polymer is crosslinked and forms a microgel when combined with water. Preferred crosslinked polyanionic polymers are chemically crosslinked. Chemical crosslinking can be by ionic or covalent bonds, preferably it is by covalent bonds. The crosslinking can be introduced at the time the polyanionic polymer is made, or it can be introduced after the polyanionic polymer is made. The chemical crosslinks can be durable under physiological conditions or they can be hydrolytically susceptible (labile) under physiological conditions. With respect to crosslinks, labile means susceptible to enzymatic or non-enzymatic hydrolysis or oxidation.

Preferably, crosslinking by covalent bonds is introduced at the time the polyanionic polymer is made by using one or more chemical crosslinking agents that have at least two ethylencically unsaturated carbon-carbon double bonds disposed to polymerize by the same mechanism as the monomers represented by structure I, preferably a free radical mechanism. Chemical crosslinking agents introduced at the time the polyanionic polymer is made can be selected to result in covalent crosslinks that will be durable under physiological conditions after application of a composition containing a polyanionic polymer. That is, the crosslinks introduced by the crosslinking agent resist break-down or scission under physiological conditions. Examples of crosslinking agents that can be introduced at the time the polyanionic polymer is made and that result in durable crosslinks include divinyl benzene and alkenyl ethers of polyhydric alcohols, for example the triallyl ether of pentaerythritol available from Aldrich Chemical (catalog 25-172-0), among others. Commercially available ethylenically unsaturated ethers or esters of those polyhydric alcohols having 3 or more hydroxyl groups typically are provided as a mixture in which some of the hydroxyl groups may be underivatized. Reference herein to a particular degree of etherification or esterification, for example tri- or tetra-, will be understood to also refer to commercially important mixtures of etherified or esterified polyhydric alcohols as are known in the art to include minor amounts of etherified or esterified polyhydric alcohols having a lower or higher than indicated degree of etherification or esterification. Thus, reference to a particular mole fraction of double bonds will be understood to encompass the variation expected because of this known variation in the degree of derivatization.

In practicing certain embodiments of the invention, for example, preferred methods of inhibiting adhesions, the crosslinks between chains of polyanionic polymer are capable of breaking-down under physiological conditions. According to one theory, break-down of the crosslinks can facilitate eventual elimination of the polyanionic polymer from the animal being treated because fragments of reduced molecular size (molecular weight) are formed when the crosslinks break down and the smaller fragments are more easily eliminated (Yamaoka et al., J. Pharm. Sci, 84, 349 (1995). Break-down of the crosslinks is facilitated if the two or more ethylenic double bonds of the crosslinking agent are separated by functional groups, for example esters or amides, that are disposed to hydrolysis. Examples of crosslinking agents having ester linkages include acrylates and methacrylates of dihydric and polyhydric alcohols such as ethylene glycol, diethylene glycol, pentaerythritol, glycerol, and sorbitol. Such crosslinking agents are either commercially available (e.g., pentaerythritol triacrylate, Aldrich Chemical catalog 24,679), or can be readily prepared from the polyhydric alcohol and acryloyl or methacryloyl chloride. Acrylates and methacrylates of polyethylene glycols having molecular weights between 200 and 40,000 can also be used as crosslinking agents. Ethylenically unsaturated derivatives of oligosaccharides, or their reduction products, can be used as crosslinkers. A particularly preferred crosslinking agent of this type is allyl sucrose. Crosslinking agents in which there is at least one carbonate or carbamate group between each ethylenic double bond and any other ethylenic double bond of the crosslinking agent can also be used. Bis-(2'-acryloxyethyl)carbonate, pentaerythritol tri(2'-acryloxyethyl)formate, and N-(2-acryloxy) ethyl-(2-acryloxy)ethyl carbamate are examples of carbonate-linked and carbamate-linked crosslinking agents. Crosslinked polyanionic polymers having hydrolytically susceptible crosslinks can also be prepared with crosslinking agents in which the ethylenic double bonds are linked by urea groups. N,N'-di(2'-acryloxyethyl)urea is an example of a urea-linked crosslinking agent. Crosslinking agents based on lactic acid can also be used. 1-(2-acryloxypropanoyl)-2-acryloxy ethane is an example of such a crosslinking agent.

Crosslinking by non-durable covalent bonds can be introduced after the polyanionic polymer is made by functionalizing the polyanionic polymer and reacting it with a suitable crosslinking agent. For example, when Y of structure I is a carboxyl group, from 0.1% to 10% of the carboxyl groups in the polymer can be functionalized to the acid chloride by, for example, the action of thionyl chloride. The acid chloride groups so formed can be reacted with, for example, an $\alpha,\omega$-diamine or $\alpha,\omega$-diol, for example a polyethylene glycol, to form covalent crosslinks through amide or ester groups on different polymer chains. Crosslinking can also be introduced after the polyanionic polymer is formed by providing pendant hydroxyl groups on the polyanionic polymer and reacting these with a bischloroformate, for example the bischloroformate of an $\alpha,\omega$-diol. The polyanionic polymer can be provided with pendant hydroxyl groups by polymerizing one or more monomers of structure I with vinyl acetate, followed by hydrolysis of the acetate groups, or by copolymerizing one or more monomers of structure I with, for example, hydroxyethylmethacrylate (HEMA). Generally, the amount of vinyl acetate or HEMA copolymerized will be sufficient to provide 0.1 to 10 hydroxyl groups per 1000 repeat units on a moles basis.

Preferably the amount of crosslinker is kept low. Preferred crosslinked polyanionic polymers form microgels with water and are made by polymerization of a mixture of one or more monomers of structure I and one or more ethylenically unsaturated crosslinking agents of the type discussed above. The amount of crosslinking agent or agents used is effective to produce a crosslinked polyanionic polymer that forms a microgel when combined with water. When ethylenically unsaturated crosslinking agents are used to form crosslinks at the time of making the polyanionic polymer, the ethylenic double bonds of the one or more ethylenically unsaturated crosslinking agents preferably account for less than 0.02 mole fraction and preferably less that 0.01 mole fraction of all ethylenically unsaturated double bonds in the combination of one or more monomers and one or more crosslinking agents. Typically, the ethylenically unsaturated crosslinking agent account for 0.001 mole fraction or more of all ethylenically unsaturated double bonds in the combination of one or more monomers and one or more crosslinking agents. These mole fractions are calculated on the basis of the nominal number of ethylenic double bonds in the ethylenically unsaturated crosslinking agent and are adjusted for the known variation in the average number of double bonds per molecule of commercially available ethylenically unsaturated crosslinking agents as discussed above.

In certain embodiments, the polyanionic polymer employed in the practice of the method of the invention has an acid number of at least about 100, more preferably at least about 200, yet more preferably at least about 400, still yet more preferably at least about 600, still more preferably at least about 700, when the polymer is in a commercially acceptable "dry" preparation such as a preparation containing the polymer and for example up to 2% moisture, residual solvent, or residual monomer. In preferred embodiments, the polyanionic polymer has 0.001 moles or more, preferably 0.0014 moles or more, more preferably 0.014 moles or more, of base titratable functional groups per gram of polymer in a commercially acceptable dry formulation.

The polyanionic polymers preferably have, in a 0.5% w/v neutralized aqueous solution (e.g. pH between 6 to 8), a Brookfield RVF or RVT viscosity, which is a measure of macroviscosity, of at least about 2,000 cP, more preferably at least about 4,000 cP (20 rpm at 25° C.). These viscosity parameters are with respect to the acid form of the polymers. See, R. Y. Lochhead et al., *Polymers in Aqueous Media*, pp. 113–147, 1989 on macroviscosity (Brookfield viscosity) and microviscosity of polymer solutions. However, in certain preferred embodiments, the macroviscosity is no more than about 100,000 times greater than the microviscosity, preferably no more than about 10,000 times greater.

In certain embodiments, the crosslinked polyanionic polymer is a crosslinked homopolymer or copolymer of acrylic acid, such as the polymers sold by the BFGoodrich Company, Specialty Polymers and Chemicals Division (Brecksville, Ohio) under the tradename Carbopol, such as carbopol 971P, Carbopol 934P and Carbopol 974P, which are preferred in the order: 971P more than 934P; and 934P more than 974P. These types of polymers have a substantially acyclic aliphatic backbone and have been termed carboxypolymethylenes or carbomers, which can be composed of any suitable number of monomers, and in a particular treatment, can be of a uniform number of such monomers or of a variable number of monomers per preparation applied to an area affected by a wound. Additionally, carboxypolymethylene can have a variable number of carboxyl groups attached to the polymethylene backbones. As crosslinker, the triallyl ether of pentaerythritol (at 0.1% to 2.5%, w/w, based on other monomers) is suitable.

Suitable salts can be, where a microgel is employed, combined with a microgel, the suitability of which is determined by the requirement that the microgel itself not cause harm to the injured cornea, peritoneum, or any other tissue with which the microgel comes in contact. Suitable salts include, but are not limited to, potassium or sodium chloride, particularly when provided at physiological concentrations, as are known in the art.

A composition used in the practice of the method of the invention can include glycerol, the carboxypolymethylene, and distilled water, and is adjusted as to pH using a base such as sodium hydroxide potassium hydroxide, alkyl amines such as diisopropanolamine (DIPA), and the like. A stock solution of a suitable concentration of glycerol can be prepared with distilled water, and is preferably an 87% (w/w) glycerol solution, the remainder of which is distilled water. A stock solution of a suitable solution of base such as sodium hydroxide can also be prepared with distilled water, for example, a 10% (w/w) sodium hydroxide solution, the remainder of which is water. By making appropriate dilutions of stock solutions, as is well known in the art, the polymer composition useful in the practice of the present method preferably has the following ranges of end concentrations of the ingredients: (1) glycerol, from about 0 to about 60% (w/w); (2) carboxypolymethylene, from about 0.1% to about 10% (w/w), more preferably from about 0.4% to about 7%, yet more preferably, from about 1% to about 5%; the remainder of the formulation being distilled water. Sodium hydroxide, 10% stock, is used for pH adjustment, resulting in an essentially neutral prepared pH, more preferably a pH from about 7 to about 7.8, yet more preferably a pH from about 7.2 to about 7.6.

When inclusion of a multifunctional hydrolase is contemplated, the polyanionic polymer composition can also be prepared with excipients intended to protect the multifunctional hydrolase upon freeze drying or upon the reconstitution thereof with distilled water, or both. Such excipients include, for example, calcium chloride, glycine, citric acid, sorbitol, and dextran. A vial that contains, for example, 50 units of the multifunctional hydrolase (which units are defined above) when freezedrying is contemplated, preferably includes the following excipients in the range of concentration given: (1) calcium chloride, from about 0.6 mM to about 1 mM, (2) glycine, from none up to about 12 mM, preferably from about 6 mM to about 10 mM, most preferably about 8 mM; (3) citric acid, from none up to about 12 mM, preferably from about 6 mM to about 10 mM, most preferably about 8 mM; (4) sorbitol, from about 100 mM to about 200 mM, preferably between about 150 mM and 170 mM, most preferably about 160 mM; and (5) dextran, from about 1% to about 10% by weight, preferably between about 7% to about 8% by weight, most preferably 6% by weight.

A preferred embodiment of the invention provides for treatment of wounds, especially cutaneous wounds, with an above described polyanionic polymer composition, optionally combined with a suitable multifunctional hydrolase. The multifunctional hydrolase preferably has proteolytic activity corresponding to that of at least one from the group comprising a chymotrypsin, trypsin, collagenase, elastase and exo peptidase activity. More preferably, the multifunctional hydrolase has at least two of said proteolytic activities; yet more preferably, at least three of said proteolytic activities; even more preferably, at least four of said proteolytic activities; and most preferably, all of said proteolytic activities.

The compositions used in the context of the method of the invention can be applied to the area to be so treated, for example topically. Polyanionic polymer compositions can be applied as paste, jelly, or in sheets that can be prehydrated or hydrated in situ by bodily fluids.

For administration to an area affected by internal trauma, for example an internal surgical wound that is susceptible to giving rise to adhesions, polyanionic polymer compositions can be administered as a paste, jelly, or pourable liquid formulation. For treatment of internal trauma, multifunctional krill-derived protein can be administered in a pharmaceutically acceptable vehicle, for example isotonic saline solution. The multifunctional protein can also be administered to an area affected by an internal surgical wound in a composition that includes a polyanionic polymer. In preferred embodiments, the multifunctional protein is administered to the area affected by a surgical wound in a composition that contains a microgel. A particularly preferred microgel contains a crosslinked polyanionic polymer. Crosslinked carboxypolymethylene is a useful crosslinked polyanionic polymer.

The method of treating trauma to a membrane, for example the peritoneum, pleura, or pericardium, or for treating trauma to an internal organ, comprises interoperatively administering a composition of the invention to the site of the trauma and the affected area. Treatment to suppress formation or reformation of surgical adhesions is performed interoperatively.

Treatment of corneal wounds can be effected using hydrolase in any pharmaceutically acceptable vehicle according to standard pharmaceutical practice. The vehicle can be a microgel. Treatment is effected by application of drops or a gel to the eye. For ocular administration, ointments or droppable liquids may be delivered by ocular delivery systems known to the art such as applicators or eye droppers. Such compositions for treatment of corneal wounds can include mucomimetics such as hyaluronic acid, chondroitin sulfate, hydroxypropyl methylcellulose or polyvinyl alcohol, preservatives such as sorbic acid, EDTA or benzylchronium chloride, and the usual quantities of diluents and/or carriers. In preferred embodiments, the composition containing multifunction protein to be administered to the eye includes a polyanionic polymer composition.

The method of treating a corneal ulcer, such as one caused by a Herpes keratitis infection, for example, preferably comprises administering to an affected eye a composition comprising the multifunctional hydrolase, wherein a corneal ulcer treating effective amount of the multifunctional hydrolase is administered, and wherein the multifunctional hydrolase preferably has at least two of a chymotrypsin, trypsin, collagenase, elastase or exo peptidase activity, and at least about 60% sequence similarity with a reference sequence. More preferably, the hydrolase has at least three of said proteolytic activities and at least about 80% sequence identity with the reference sequence. Yet more preferably, the hydrolase has at least three of said proteolytic activities and at least about 90% sequence similarity with the reference sequence. Even more preferably, the hydrolase has at least three of said proteolytic activities and at least about 90% sequence identity with the reference sequence. Yet even more preferably, the hydrolase has at least three of said proteolytic activities and at least about 95% sequence similarity with the reference sequence.

In embodiments directed to the inhibition of adhesions, the method can include pretreatment or simultaneous treatment, or both, of the traumatized membrane with corticosteroids, such as cortisone, alone or in combination with an antihistamine.

As noted above, the multifunctional hydrolase used in the context of the invention preferably is a krill-derived hydrolase, such as a proteinase. More preferably, the multifunctional hydrolase is part of a multifunctional protein, which may have non-enzymatic functions as well as enzymatic functions. Crustaceans, including antarctic krill, are useful sources for the multifunctional protein of the invention. A protein having "multifunctional activity," is defined herein as including at least one of a chymotrypsin, trypsin, collagenase, elastase or exo peptidase activity, or asialo $GM_1$ ceramide binding activity. For purification of krill-derived multifunctional protein, see below and, for example, U.S. patent application Ser. No. 08/600,273 (filed Feb. 8, 1996), deFaire et al., inventors, entitled "Multifunctional Enzyme," which is incorporated herein by reference.

For topical treatments, including treatments to internal surfaces, a preferred suitable dose of multifunctional krill-derived protein per application ranges from about 0.01 U/ml to about 10 U/ml, where typically a layer of from 0.5 to 5 mm of carrier such as cream, ointment, polyanionic polymer or the like is applied, more preferably about 0.01 U/ml to about 1.0 U/ml, still more preferably about 0.2 U/ml. This dosage range applies to vehicles such as gels, ointments, creams, liquids, sprays, aerosols, and the like. In some embodiments, such as wound debridement, larger dosages may be used initially. Lozenges preferably are designed to deliver about 0.01 U to about 10 U, more preferably about 0.01 U to about 1.0 U, still more preferably about 0.2 U. For all external treatments, the protein composition will generally be applied from about 1 to about 10 times per day, preferably from about 2 to about 5 times per day. These values, of course, will vary with a number of factors including the type and severity of the disease, and the age, weight and medical condition of the patient, as will be recognized by those of ordinary skill in the medical arts. It is believed that substantially higher doses can be used without substantial adverse effect. Generally, the multifunctional protein will be administered in an effective amount.

In another embodiment, the invention provides a method for treating trauma susceptible to giving rise to the formation of adhesions by administering to the area affected by such trauma with an effective amount of a composition that includes a polyanionic polymer (e.g., microgel). When the trauma is to the peritoneum, 200 to 300 ml of polymer composition containing 0.5% to 2.5% by weight polyanionic polymer is a typical effective amount, but the practitioner will know to modify this amount according to the location, size, and severity of the trauma.

Humans are the preferred subjects for treatment. However, the multifunctional protein can be used in many veterinary contexts to treat animals, preferably mammals, as will be recognized by those of ordinary skill in light of the present disclosure.

The composition to be administered is preferably buffered to a physiologically suitable pH, such as pH 6.5 to pH 7.5. Where an enzyme is included in the composition, salts and stabilizing agents can be added in amounts effective to increase activity or stabilize the enzyme.

In another preferred embodiment, the multifunctional hydrolase used in the context of the invention preferably has the above-described proteolytic activity and at least about 60% sequence identity or similarity with a reference sequence. More preferably, the multifunctional hydrolase has at least about 70% identity or similarity with the reference sequence; yet more preferably, at least about 80% or 85% identity or similarity with the reference sequence; even more preferably, at least about 90% or 95% identity or similarity with the reference sequence; and most preferably, at least about 97% identity or similarity with the reference sequence. While the percentage similarity noted above is preferred, the percentage identity is more preferred.

Many other administration vehicles are apparent to the artisan of ordinary skill, including, without limitation, slow release formulations, liposomal formulations and polymeric matrices.

The method of treatment of trauma by administering the polyanionic polymer composition, with or without the multifunctional hydrolase or other agents, such as antibiotics, is preferably conducted for a suitable time, the suitability of which will be known to the skilled practitioner for example from inspection of the affected tissue and the kind and severity of the condition being treated. The treatment is preferably administered at least until healing of the affected wound is complete, more preferably for at least an additional five days thereafter. Corneal wounds can be, for example, treated for 2 to 35 days. In other cases, the treatment is conducted for at least about 10 days, more preferably for at least about 20 days, yet more preferably for at least about 28 or 35 days. Treatment of cutaneous wounds with a composition containing a polyanionic polymer composition and a multifunctional hydrolase can be from 7 to 42 days. Treatments are preferably accomplished via application at least once per day, more preferably twice a day up to about six times a day, using methods of topical application to the eye as are known in the art.

The multifunctional hydrolase has a preferred molecular weight of from about 20 kd to about 40 kd; more preferably, the molecular weight is from about 26 kd to about 32 kd.

Preferred multifunctional hydrolases include, but are not limited to *Panaeus vanameii* 1, *Panaeus vanameii* 2, *Panaeus monodon* chymotryptic-1, *Panaeus monodon* tryptic, *Panaeus monodon* chymotryptic-2, *Uca pugilator* enzyme I, *Uca pugilator* enzyme II, Kamchatka crab IA, Kamchatka crab IIA, Kamchatka crab IIB, Kamchatka crab IIC, Crayfish protease 1, Salmon enzyme 1, Atlantic cod I Atlantic cod II or third Atlantic cod trypsin (described in European J. Biochem., 180: 85–94 (1989) and Protein Resource Accession No. S03570. Preferably, these specific enzymes comprise the following respective peptide sequences: *Panaeus vanameii* 1, I-V-G-G-V-E-A-T-P-H-S-W-P-H-Q-A-A-L-F-I-D-D-M-Y-F(SEQ ID NO:2); *Panaeus* vanameii 2, I-V-G-G-V-E-A-T-P-H-S-X-P-H-Q-A-A-L-F-I (SEQ ID NO:3); *Panaeus monodon* tryptic I-V-G-G-T-A-V-T-P-G-E-F-P-Y-Q-L-S-F-Q-D-S-I-E-G-V (SEQ ID NO:4); *Panaeus monodon* chymotryptic-1; I-V-G-G-V-E-A-V-P-G-V-W-P-Y-Q-A-A-L-F-I-I-D-M-Y-F (SEQ ID NO:5); *Panaeus monodon* chymotryptic-2, I-V-G-G-V-E-A-V-P-H-S-W-P-Y-Q-A-A-L-F-l-I-D-M-Y-F (SEQ ID NO:6); *Uca pugilator* enzyme I, I-V-G-G-V-E-A-V-P-N-S-W-P-H-Q-A-A-L-F-I-D-D-M-Y-F (SEQ ID NO:7); *Uca pugilator* enzyme II, I-V-G-G-Q-D-A-T-P-G-Q-F-P-Y-Q-L-S-F-Q-D (SEQ ID NO:8); Kamchatka crab IA, I-V-G-G-Q-E-A-S-P-G-S-W-P-X-Q-V-G-L-F-F (SEQ ID NO:9); Kamchatka crab IIA, I-V-G-G-T-E-V-T-P-G-E-I-P-Y-Q-L-S-L-Q-D (SEQ ID NO:10); Kamchatka crab IIB, I-V-G-G-T-E-V-T-P-G-E-I-P-Y-Q-L-S-F-Q-D (SEQ ID NO:11); Kamchatka crab IIC, I-V-G-G-S-E-A-T-S-G-Q-F-P-Y-Q-X-S-F-Q-D (SEQ ID NO:12); Crayfish protease 1, I-V-G-G-T-D-A-T-L-G-E-F-P-Y-Q-L-S-F-Q-N (SEQ ID NO:13); Salmon enzyme 1, I-V-G-G-Y-E-C-K-A-Y-S-Q-A-Y-Q-V-S-L-N-S-G-Y-H-Y-C (SEQ ID NO:14); Atlantic cod I, I-V-G-G-Y-E-C-T-K-H-S-Q-A-H-Q-V-S-L-N-S-G-Y-H-Y-C (SEQ ID NO:15); Atlantic cod II, I-V-G-G-Y-E-C-T-R-H-S-Q-A-H-Q-V-S-L-N-S-G-Y-H-Y-C (SEQ ID NO:16); or third Atlantic cod N-terminal protein sequence I-V-G-G-Y-Q-C-E-A-H-S-QA-H-Q-V-S-L-N-S-G-Y-H-Y-C-G-G-S-L-I-N-W-V-V-S-A-A (SEQ ID NO:17).

The most preferred multifunctional hydrolase used in the context of the invention is PHM-101, which is a purified preparation of a krill multifunctional hydrolase. Methods of purifying the enzyme, as well as preferred characteristics, are described in PCT/US99/14751.

The inventive method can include pretreatment or simultaneous treatment, or both, of the affected tissue with a suitable antibiotic. A suitable antibiotic is one that retains its potency when placed in physiological conditions. Some antibiotics are preferred for topical use on tissue, such as, but not limited to ciprofloxacin. The antibiotic can be included in the treatment using the polyanionic polymer with or without the multifunctional hydrolase.

6. Hydrolytically Susceptible Polymers

Provided is, in one embodiment, polyanionic polymer comprising hydrolytically susceptible bonds comprising: two or more polyanionic polymer segments; linking moieties coupling the polyanionic polymer segments, wherein the linking moieties comprise (I) or (II) below or both:.

(I) a segment joining joined via amide, ester or thioester bonds incorporating an acyl or acyl analog moiety of the polyanionic polymer, wherein the segment comprises: (a) a $C_1$ to $C_2$ alkylene (which alkylenes here and for those recited below in this paragraph can be $C_1$ to $C_{10}$ or $C_1$ to $C_5$) with terminal linkers selected from oxy, thio (—S—) or imino (—NR—, where R is H or $C_1$–$C_6$ alkyl) incorporated into the amide, ester or thioester bonds, provided that at least one of the amide, ester or thioester bonds is other than an ester bond; or (b) an amide, ester or thioester linked polymeric segment of (i) hydroxy or thiol $C_2$–$C_5$ carboxylic acid or hydroxy proline derivatives and (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) an α,ω-diol or a chain extended α,ω-diol}; or (c) an amide, ester or thioester linked polymeric segment of (i) one or more hydroxy or thiol $C_2$–$C_5$ carboxylic acid or hydroxy proline derivatives, (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) one or more α,ω-diols or chain extended α,ω-diols} and (iii) one or more carbonyldioxy moieties; or (d) an amide, ester or thioester linked polymeric segment of (ii)(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds, (ii)(b) one or more chain extended (α,ω-diols and (iii) one or more carbonyldioxy moieties; or (e) an amide, ester or thioester linked polymeric segment of (ii)(b) one or more chain extended α,ω-diols and (iii) one or more carbonyldioxy moieties; or (f) a direct anhydride formed between acid moieties of the polyanionic polymer; or (g) an anhydride bridge formed between acid moieties of the polyanionic polymer with carbonyl bridge; or (I) the residue after a crosslinking reaction of:

(a) two or more terminal acrylate or methacrylate moieties providing unsaturated bonds available for the crosslinking reaction;

(b) a segment joining the terminal acrylate or methacrylate moieties via amide, ester or thioester bonds incorporating an acyl bond of the acrylate or methacrylate moieties, wherein the segment comprises: (1) a $C_1$ to $C_{12}$ alkylene with terminal linkers selected from oxy, thio (—S—) or imino (—NR—, where R is H or $C_1$–$C_6$ alkyl) incorporated into the amide, ester or thioester bonds, provided that at least one of the amide, ester or thioester bonds is other than an ester bond; or (2) an amide, ester or thioester linked polymeric segment of (i) hydroxy or thiol $C_2$–$C_5$ carboxylic acid or hydroxy proline derivatives and (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) an α,ω-diol or a chain extended α,ω-diol}; or (3) an amide, ester or thioester linked polymeric segment of (i) one or more hydroxy or thiol $C_2$–$C_5$ carboxylic acid or hydroxy proline derivatives, (ii) {(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds or (b) one or more α,ω-diols or chain extended α,ω-diols} and (iii) one or more carbonyldioxy moieties; or (4) an amide, ester or thioester linked polymeric segment of (ii)(a) a $C_1$ to $C_{12}$ alkylene moiety with terminal linkers selected from oxy, thio (—S—) or imino (—NR—, where R is H or $C_1$–$C_6$ alkyl) incorporated into the amide, ester or thioester bonds, (ii)(b) one or more chain extended α,ω-diols and (iii) one or more carbonyldioxy moieties; or (5) an amide, ester or thioester linked polymeric segment of (ii)(b) one or more chain extended α,ω-diols and (iii) one or mole carbonyldioxy moieties.

In another embodiment, provided is a linear polyanionic polymer comprising: two or more polyanionic polymer segments each terminating at one or both ends with a linker that is an oxygen or sulfur residue from a hydroxide or thiol moiety; and linker moieties cleavable at internal amide, ester or thioester bonds linking the linkers to form the linear polyanionic polymer. The polymer can comprise a monomer moiety which consists of atoms selected from carbon, hydrogen, oxygen and sulfur and comprises carbon and hydrogen.

In one embodiment of the invention, (a) a core which is a $C_1$ to $C_{12}$ (preferably $C_1$ to $C_{10}$ or $C_1$ to $C_5$) alkylene with three or more (e.g., up to 5 or 6) linking hydroxyls or thiols or a mono or disaccharide with three or more linking hydroxyls is reacted with (b) three or more (e.g., eight) equivalents of a cyclic diester of the following formula:

(52)

in which $R^1$ and $R^2$ are independently methylene or ethylene which can be substituted with up to two $C_1$ to $C_4$ alkyls. The resulting multivalent core has a structure with substituents at the former hydroxyls or thiols which are $—R^3{}_n$, where n is zero or more (such as zero to eight) with the total sum of the n values being at least three to eight (such as three to eight), and $R^3$ is independently:

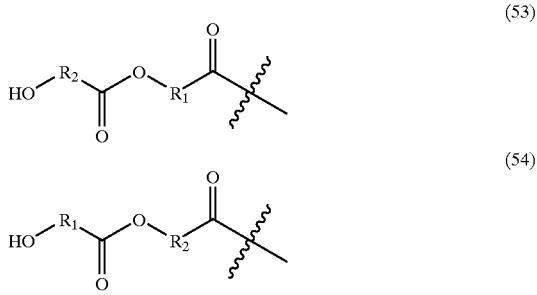

(53)

(54)

Preferably, $R^1$ and $R^2$ are methylene, which can be substituted. Preferably, the substitution is $C_1$ to $C_2$ alkyl. The terminal hydroxyls from the opened cyclic diester are reacted to substitute the hydroxyl with an ester or ether-linked unsaturated moiety adapted to be reactive in a subsequent free-radical polymerization (which in turn in adapted to yield polyanionic polymer segments). Preferably, this moiety is a ester-linked acryloyl radical, as can be formed for example with acryloylchloride. The average of n is preferably 1 or 2. Preferably, at least 80%, 90%, 95% or 98% or more of the of the linking hydroxyls or thiols of the core are so reacted. One preferred core is pentaerythritol.

Starting with any multivalent core (such as any described herein) having terminal unsaturated moieties adapted to be reactive in a subsequent free-radical polymerization, the subsequent free radical polymerization is preferably adapted to limit (e.g., with a chain terminator) the polyanionic polymer segments to molecular weights for 90% or more of the segments of 50 kd or 40 kd or less. In one embodiment, 95% or 98% or more of the segments fall within these size limits. Preferably, the average molecular weight is from 20 kd to 40 kd, or 25 kd to 35 kd. Appropriate chain terminators are known in the art.

Thus, in one embodiment of the invention, the polyanionic polymer has polyanionic segments of these sizes crosslinked with multivalent crosslinkers containing hydrolytically susceptible bonds.

Core moieties can be reacted with compounds of formula (52) at an elevated temperature effective to melt such compounds of formula (52), such as 120° C. for lactide, and the reaction conducted over, for example, an 20 or more hours. An example of forming the linked moieties adapted to be reactive in a subsequent free-radical polymerization is reacting with acryloylchloride in dichloromethane in the presence of triethylamine at ambient temperature.

Other preferred hydrolytically susceptible polymers polyailionic polymers include any in which comprise two or more linearly linked polyanionic segments, where the linkages are through hydrolytically susceptible linking moieties connecting to terminal oxo or thio moieties of the polyanionic segments, such as those described below under Approach IV. Preferably, the segments fall within one or more of the size restraints described here. These linear multimers of polyanionic segments can be further crosslinked with hydrolytically susceptible linking moieties.

In other preferred hydrolytically susceptible polymers polyanionic polymers, containing carboxylates, for which a sampling of the carboxylate-providing monomers (e.g., 1 of 20) are derivatized to attach $—X—R^4—Y—H$ via an amide, ester or thioester bond, where X and Y are independently S, O or NH and $R^4$ is a straight chain $C_1–C_{10}$ (preferably $C_1–C_5$) alkyl which can be substituted with up to two $C_1–C_4$ alkyls. Preferably, X and Y are different to provide differential reactivities that facilitate selective addition of one end to the polyanionic polymer. However, protecting group chemistry (Ser. No. 09/644,121) can be used to achieve this selective attachment even if X and Y are the same. YH in turn reacts by Micheal addition with a crosslinkers (linking moieties) with terminal acrylate or acrylamide moieties. Thus, the linking moiety has the structure:

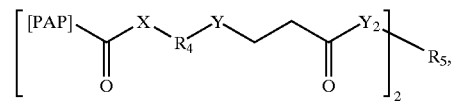

where $Y^2$ is S, O or NH (preferably O or NH), n is 2 or more (e.g., up to 4, 5 or 6) and $R^5$ is an hydrolytically susceptible linking moiety comprising C, H and two or more heteroatoms which can be O, S or N, the O, S and N atoms all participating in hydrolytically susceptible bonds or ether or thioether bonds. $R^5$ can be or include a segment of PAP (such as PEG), which preferably has molecular weight within the above-described preferred ranges. Aside from PAP, which may not be present, $R^5$ preferably has molecular weight of less than 5,000, more preferably less than 1,000. A large number of examples of $R^5$ are described herein.

The polymers crosslinked with the linking moieties described in the preceding text of this Section 6 or with hydrolytically susceptible bonds and the polyanionic polymer segments sizes described in the preceding text of this Section 6 are "polymers."

The linking agents or linking moieties of the invention can be obtained via a variety of approaches, such as those detailed below. Generally, most of the linking agents or linking moieties are used to create polymers according to the following:

Approach I

Formation of degradable cross-linked PAP during free-radical polymerization.

Carbomers are formed presently by polymerization of acrylic acid in the presence of a degradable crosslinking agent. The contributions of this Approach I come by design of linking moieties to yield hydrolytically degradable hydrogels. One or more hydrolytically susceptible links are placed within the crosslinking agent, e.g. between the sites of polymerizable unsaturation. This is contrasted with the crosslinking agent that is used in commercial Carbomers, (1), which is designed to be hydrolytically stable:

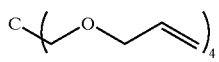
(1)

In these polymers, it may be advantageous to polymerize the anionic monomers under conditions that the PAP MW is relatively low, approximately 50,000 and less, for example, using chain transfer agents or with high concentrations of initiator.

I.A.

Degradable linking moieties based on pentaerythritol cores:

To achieve degradability, one seeks to incorporate bonds that are known to be hydrolytically susceptible within the linking moiety, such as esters, amides, carbonates, ureas, and the like. For example, one can incorporate (2), which can be prepared by reaction of pentaerythritol with acryloylchloride:

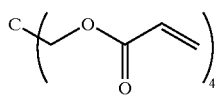
(2)

A linking agent that contains both a carbonate and an ester, which can be expected to degrade faster than (2), can be prepared from pentaerythritol and hydroxyethylacrylate linked with phosgene:

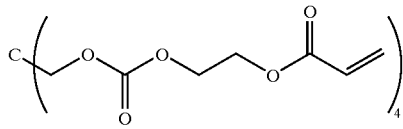
(3)

Naturally, the above can be made from a variety of cores, such as 1,2-ethanediol, or from glycerol, or from triethanolamine, or from other cores that can be identified by those skilled in the art.

I.B.

Degradable linking moieties based on two or more unsaturated sites of polymerization, for example, materials from hydroxyethylacrylate (4) and/or aminoethylacrylate (5):

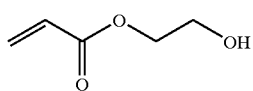
(4)

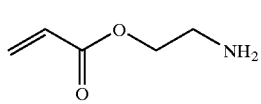
(5)

For example, dimerization of (4) and (5) with phosgene will yield at least one of the following, depending on the dimerized pair:

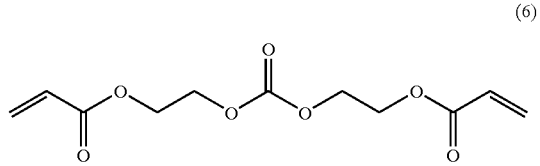
(6)

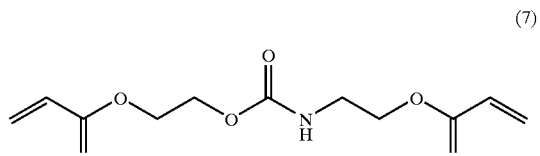
(7)

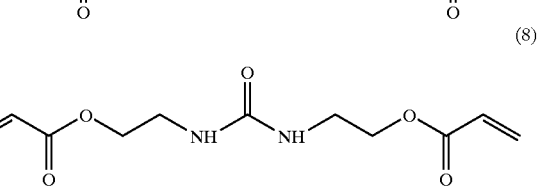
(8)

One can expect (6) to degrade faster than (7), and (7) to degrade faster than (8). One can make analogous structures with more than two unsaturated sites of polymerization.

I.C.

Degradable linking moieties based on materials from acryloylchloride (9):

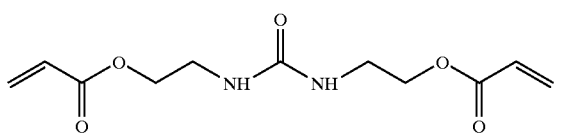
(9)

Dimerization of (9) with 1,2-ethanediol yields (10), which is hydrolytically susceptible:

(10)

Dimerization of (9) with ethanolamine yields (11), which can be expected to degrade slower than (10):

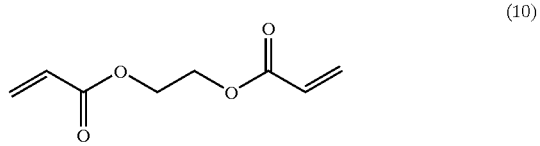
(11)

Dimerization of (9) with 1,2-diaminoethane yields (12), which can be expected to degrade slower than (11):

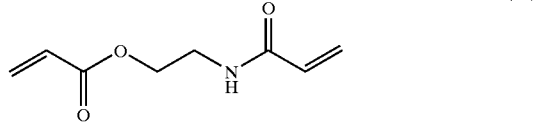
(12)

Alternatively, one can form the anhydride crosslinking agent, which can be expected to degrade faster than (10):

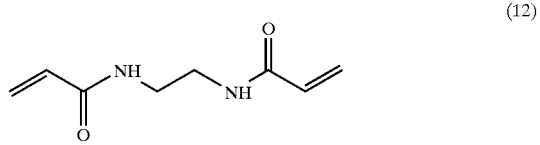

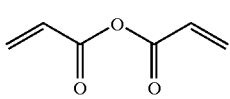
(13)

I.D.
Degradable linking moieties based on lactic acid or other hydroxy acids:
I.D.1.
One can react lactic acid (14)

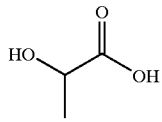
(14)

with acryloylchloride to form (15):

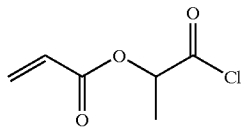
(15)

(15) can then be reacted with hydroxyethylacrylate to form (16):

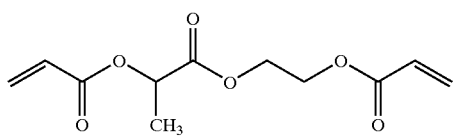
(16)

One can make such structures with more than two unsaturated sites of polymerization as well.
I.D.2.
One can also use lactyl esters, i.e. dimers of lactic acid, or dimers of other hydroxy acids. For example, one can take hydroxyethylacrylate and employ the hydroxyl to ring open lactide under non-polymerizing conditions to yield (17):

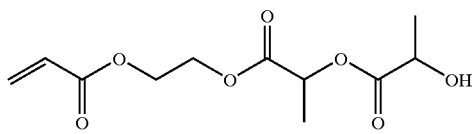
(17)

17) can be reacted with acryloylchloride to form the linking agent (18):

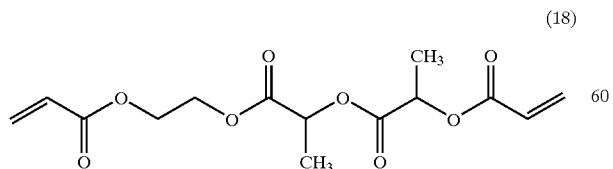
(18)

Like structures can be formed with more than two unsaturated sites of polymerization and with other hydroxy acids.
I.E.
Linking agents containing PAO diols (19) or other multifunctional PAOs, or other difunctional or multifunctional water soluble polymers, of which PEG is exemplary, as illustrated in a number of exemplary structures below:

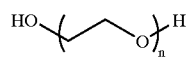
(19)

Such approaches are advantageous in that the MW of the PAO can be altered to gain a second approach to control of the physical characteristics of the hydrogel particles. Higher MW PAOs yields lower degrees of cross-linking.
I.E.1.
With PAO diols:
One can form the carbonate-containing linking agent by linking PAO to hydroxyethylacrylate with phosgene, to obtain (20):

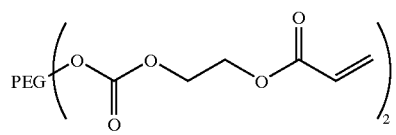
(20)

Alternatively, the ester-containing group can be obtained by reacting PAO with acryloylchloride to obtain (21)

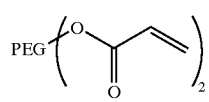
(21)

One can incorporate lactic acid esters such as be reacting PAO diol with lactic acid and phosgene to form (22):

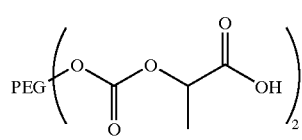
(22)

The acid chloride of (22) is formed and reacted with hydroxyethylacrylate to obtain (23):

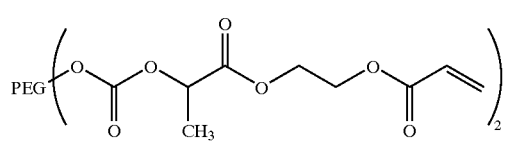
(23)

One can activate the hydroxyl of PAO diol to form an ester with lactic acid (24):

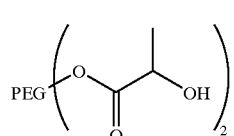
(24)

(24) is then reacted with acryloylchloride to obtain (25):

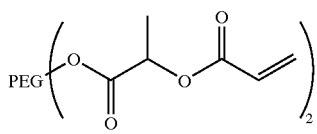
(25)

One can alternatively link a pair (or more) of lactic acid residues, by a ring-opening reaction with lactide to obtain (26):

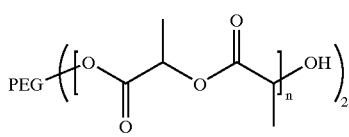
(26)

where n is preferably 10 or less, more preferably 5 or less. (26) can be acrylated to yield (27);

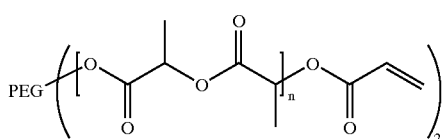
(27)

Alternatively, one can couple (26) to hydroxyethylacrylate to obtain (28):

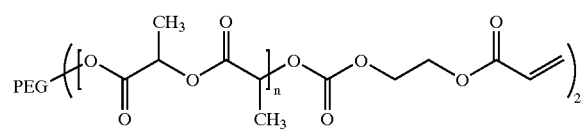
(28)

I.E.2.

Polymers made with PAO diamines:

Analogous amide and urea structures can be obtained from PAO diamine. In general, these structures will degrade more slowly than their ester and carbonate analogues.

Approach II

Linking or cross-linking of shorter PAP chains with PAO chains, employing a degradable linker between the two:

The polymerization of PAP chains in the absence of cross-linking, and then cross-linking them thereafter, provides facile control over PAP MW and thus over the pharmacodynamics of the degradation products of the cross-linked polymer particles.

II.A.

Polymers made from poly(AM-co-hydroxyethylacrylate):

Small amounts of hydroxyl can be included along the PAP chain, for example, by co-polymerization of anionic monomer with hydroxyethylacrylate ($H_2C=CHCO_2CH_2CH_2OH$) or by copolymerization with vinyl acetate, followed optionally by then hydrolysis of the acetyl side group to yield the additional alcohol. The hydroxyl side groups can be cross-linked by reaction with PAO diol activated with phosgene to yield (29):

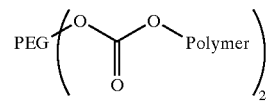
(29)

II.B.

Polymers made from PAP:

Alternatively, one can begin with PAP, derivatize some of side-chain carboxyl groups (or analogous groups) with aminoethane thiolgroups, and cross-links these with a degradable diacrylate linking agent, for example, (21) to yield (30):

(30)

PEG—(O—C(O)—CH₂CH₂—S—CH₂CH₂—NH—C(O)—Polymer)₂

II.C.

Polymers containing both carbonate and ester links:

One can start with PAP, convert some of the carboxyl side groups (or analogous groups) to the acid chloride, and functionalize these with 1,2-ethanediol under non-cross-linking conditions. This material can be cross-linked with PAO diol that has been pre-activated with phosgene, to yield (31):

(31)

PEG—(O—C(O)—O—CH₂CH₂—O—C(O)—Polymer)₂

(31) can also be formed from the copolymer with hydroxyethylacrylate and then coupling with PAO after activation of the PAO with phosgene.

II.D.

One can incorporate lactic acid, or other hydroxy acids, in the linkers from the hydroxyl-containing copolymer (shown here from the hydrolysis product of a copolymer with vinyl acetate) after ring opening of lactide under non-polymerizing conditions to obtain (32):

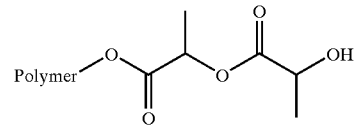
(32)

(32) can then be coupled with phosgene-activated PAO diol to obtain (33):

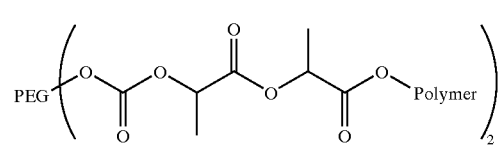
(33)

One can also use the PAO terminal hydroxyls to ring open lactide under non-polymerizing conditions to yield a diol precursor and couple this to phosgene-activated PAO diol to obtain (34):

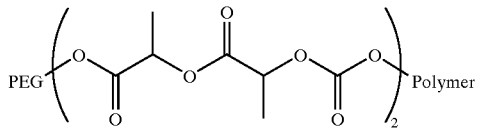

(34)

Approach III

Cross-linking of PAP:

As in Approach II, one can cross-link or link PAP after polymer-forming reaction.

III.A.

For example, one can start with PAP, form a small fraction of the acid chloride, and cross-link with 1,2-ethanediol, or a similar diol, to obtain (35):

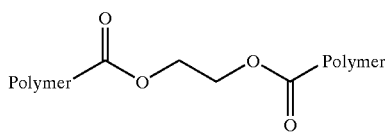

(35)

III.B.

One can start with a hydroxyl-containing copolymer and cross-link with phosgene, to obtain (36):

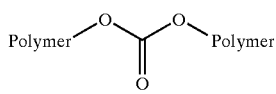

(36)

Alternatively, the anhydride linked material may be obtained directly (37)

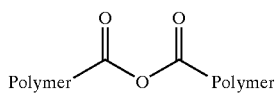

(37)

III.C.

One can use a lactide ring-opening reaction, for example, with 1,2-ethanediol in excess, to obtain (38):

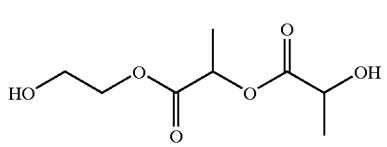

(38)

(38) can be used to cross-link a phosgene-activated homopolymer to obtain (39) or with an acid-chloride activated homopolymer PAP to obtain (40):

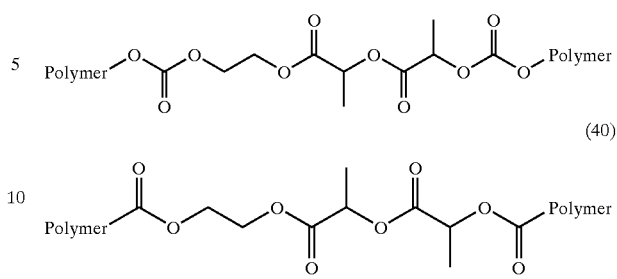

(39)

(40)

Approach IV

Hydrolytically susceptible (i.e., unstable) linear PAP.

Coupling of short PAP chains via degradable moieties can be used to obtain a linear PAP with a high molecular weight.

IV.A.

Degradable linear PAP from hydroxyl terminated PAP.

One can polymerize anionic monomer via living polymerization and obtain low molecular weight PAP with terminal hydroxyl groups (41):

(41)

Coupling of the hydroxyl groups with phosgene results in an extended PAP chain linked by degradable carbonate groups (42):

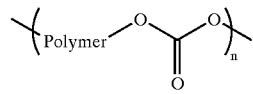

(42)

The size of the degradable block can be increased by reaction of hydroxyl terminated PAP with, for example, a PAO diol, activated by phosgene to yield (43):

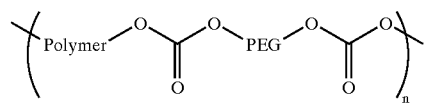

(43)

One can also use (41) in a lactide ring opening reaction under non-polymerizing conditions to obtain (44):

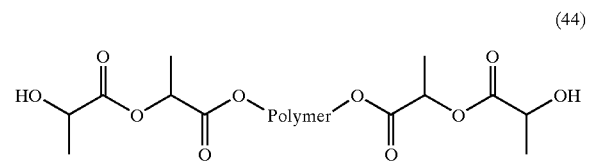

(44)

Subsequently, the hydroxyl groups of 2 such polymer segments can be reacted with 1,1'-carbonyldiimidazole (CDI) (or phosgene can be used) to obtain a high molecular weight PAP composed of PAP blocks separated by lactyl moieties, for example, (45):

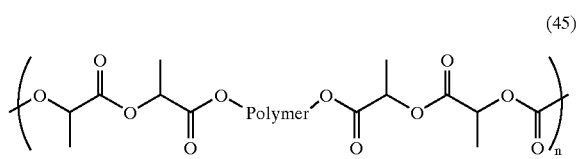

(45)

Alternatively, (44) can be coupled to (41) in this way, yielding (46):

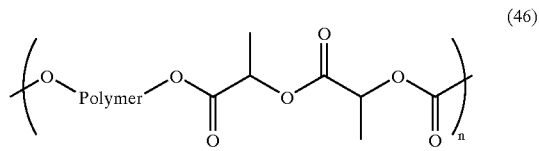

(46)

IV.B.

Degradable linear PAP from PAP segments.

As in IV.A, one can obtain low molecular weight PAP via living polymerization with other terminal groups than hydroxyl groups, for example, thiol groups (47)

(47)

These groups can be reacted with diacrylated compounds, as described in II.B, for example, with a PAO-diacrylate (21) to obtain (48):

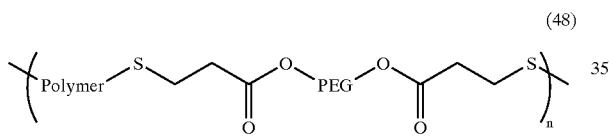

(48)

Reacting (47) with shorter degradable blocks, for example, diacrylates (10), (11), and (12) from I.C., one can expect to obtain polymers (49), (50), and (51) with different degrees of degradation susceptibility:

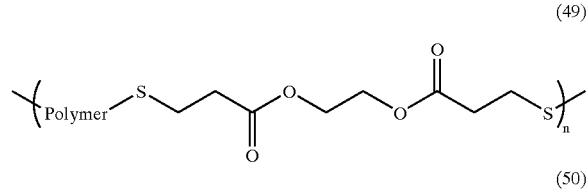

(49)

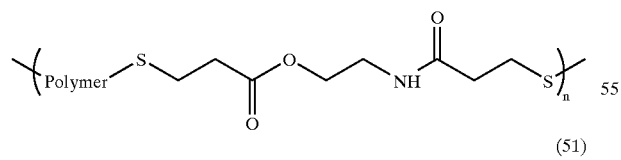

(50)

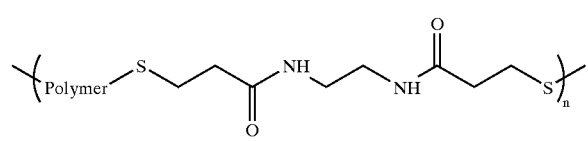

(51)

The various polymers described herein are presented in greater detail in an application filed concurrently herewith (Ser. No. 09/644,121).

EXAMPLE

This example sets forth methods for preparing hydrogel and microgel used in the context of the present invention. The microgel is used by itself or in combination with other agents, such as the krill-derived multifunctional hydrolases also set forth herein.

The chemicals and materials used therefor were: Glycerol (Merck, Darmstadt, GERMANY), Carbopol® polyanionic polymers (BFGoodrich Company, Specialty Polymers and Chemicals, Brecksville, Ohio), diisopropanol amine (Aldrich), distilled water, and 10% sodium hydroxide. The final concentrations of the component chemicals were: 23.5% w/v Glycerol stock (which is 87% w/w); 0.8% w/v of the desired polyanionic polymer; and distilled water and the sodium hydroxide (10%) or diisopropanol amine used to adjust the pH to 7.4 and make to volume.

Using standard sterile procedures, the carbopol was mixed in small amounts with distilled water under slow agitation with a propeller stirrer. The stirring continued until the powder was dissolved. Any trapped air was removed by reducing the pressure (water operated vacuum gauge). Glycerol was added under slow stirring and the pH was measured, and the 10% NaOH solution or the diisopropanol amine was used to adjust the composition to pH 7.4. Gelation occurred, resulting in a clear, transparent microgel. The resultant microgel was stored at 4° C.

Using the same methodology, but with weight to weight measurements of amounts, the following 10 g batches were made:

| Batch 1 | |
| --- | --- |
| Xanthan gum* | 0.6 g |
| Glycerol | 2.058 g |
| sodium hydroxide pellets | quantity sufficient |
| sterile water | quantity sufficient |
| Batch 2 | |
| Carbopol 934P | 0.08 g |
| Glycerol | 2.058 g |
| sodium hydroxide (10% w/w) | quantity sufficient |
| sterile water | quantity sufficient |
| Batch 3 | |
| Carbopol 934P | 0.04 g |
| Glycerol | 2.058 g |
| 40% w/w diisopropanolamine | quantity sufficient |
| sterile water | quantity sufficient |
| Batch 4 | |
| Carbopol 971P | 0.25 g |
| Glycerol | 2.058 g |
| 40% w/w diisopropanolamine | quantity sufficient |
| sterile water | quantity sufficient |
| Batch 5 | |
| Carbopol 974P | 0.08 g |
| glycerol | 2.058 g |
| 40% w/w diisopropanolamine | quantity sufficient |
| sterile water | quantity sufficient |

*Keltrol-T brand, supplied by Monsanto,

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed is:

1. A method of treating an area affected by a trauma selected from corneal wounds and internal trauma comprising administering to the affected area a trauma treating effective amount of a composition comprising a polyanionic polymer that is a microgel comprising polymer strands formed from at least one ethylenically unsaturated monomer, wherein the polymer strands are linked by at least one linking moiety comprising a hydrolytically susceptible bond.

2. The method of claim 1, wherein when the internal trauma is susceptible of giving rise to post-traumatic adhesions, the polymer is pre-formed.

3. The method of claim 1, wherein the corneal wound is a corneal ulcer, a corneal abrasion, or a chemical or physical insult to the cornea susceptible to giving rise to a corneal ulcer.

4. The method of claim 1, wherein the internal trauma (a) is an internal surgical wound, (b) comprises a trauma to a membrane that covers either an internal organ or tissue or the cavity in which one or more internal organs or tissues reside or (c) is susceptible of giving rise to adhesions and the amount of polyanionic polymer administered is an amount effective to inhibit or reduce formation or reformation of adhesions.

5. The method of claim 1, wherein the polyanionic polymer is a pre-formed, hydrolytically susceptible non-addition polymer comprising polymer strands formed from at least one ethylenically unsaturated monomer, wherein the polymer strands are linked by at least one linking moiety comprising a hydrolytically susceptible bond, wherein at least one of which monomers has:
   i) one or more functional groups that can be titrated with base to form negatively charged functional groups, or
   ii) one or more precursor groups that are precursors of the functional groups that can be titrated with base; which precursor groups are converted to the functional groups.

6. The method of claim 5, wherein the functional groups are selected from $-C(O)OR^4$, $-O-S(O_2)OR^4$, $-S(O_2)OR^4$; or $-S(O)OR^4$; wherein $R^4$ is hydrogen, and wherein precursor groups are selected from $-C(O)OR^4$, $-O-S(O_2)OR^4$, $-S(O_2)OR^4$, or $-S(O)OR^4$; wherein $R^4$ is independently a $C_1-C_6$ normal or branched alkyl, phenyl, or benzyl group.

7. The method of claim 6 wherein the one or more ethylenically unsaturated monomers is according to the formula:

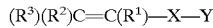

wherein:
Y is $-C(O)OR^4$; $-O-S(O_2)OR^4$; $-S(O_2)OR^4$; or $-S(O)OR^4$; wherein $R^4$ is hydrogen or a cleavage permitting group;
X is a direct bond; a straight or branched alkylene group having two to six carbon atoms, one or more of which can be replaced by O, S, or N heteroatoms, provided that there is no heteroatom in a position $\alpha$ or $\beta$ to Y; phenylene; a five or six membered heteroarylene having up to three heteroatoms independently selected from O, S, and N, provided that neither Y or $R^3\ R^2C=C(R^1)-$ is bonded to a heteroatom; and
$R^1$, $R^2$, and $R^3$ are independently selected from, hydrogen, $C_1-C_6$ alkyl, carboxy, halogen, cyano, isocyanato, $C_1-C_6$ hydroxyalkyl, alkoxyalkyl having 2 to 12 carbon atoms, $C_1-C_6$ haloalkyl, $C_1-C_6$ cyanoalkyl, $C_3-C_6$ cycloalkyl, $C_1-C_6$ carboxyalkyl, aryl, hydroxyaryl, haloaryl, cyanoaryl, $C_1-C_6$ alkoxyaryl, carboxyaryl, nitroaryl, or a group $-X-Y$; wherein $C_1-C_6$ alkyl or $C_1-C_6$ alkoxy groups are either linear or branched and up to Q-2 carbon atoms of any $C_3-C_6$ cycloalkyl group, wherein Q is the total number of ring carbon atoms in the cycloalkyl group, are independently replaced with O, S, or N heteroatoms; with the proviso that neither doubly-bonded carbon atom is directly bonded to O or S; and wherein aryl is phenyl or a 5 or 6 membered heteroaryl group having up to three heteroatoms selected from the group consisting of O, S, and N.

8. The method of claim 1, wherein the polyanionic polymer has one or more pendant first functional groups selected from hydroxy, acyl halide, chloroformate, and mercapto; and wherein the polyanionic polymer is crosslinked by reaction of a crosslinking agent having second functional groups reactive with the first functional groups.

9. The method of claim 1, wherein the polyanionic polymer is crosslinked with a crosslinking agent that comprises an ethylenically unsaturated derivative of a multidentate compound, comprising two or more two or more ethylenically unsaturated moieties, each such moiety being linked to the multidentate compound through a hydrolytically susceptible bond.

10. The method of claim 1, wherein the composition further comprises a trauma treating effective amount of a protease.

11. A method of treating a wound comprising administering to the affected area an effective amount of a composition comprising a microgel that is a pre-formed first polyanionic polymer wherein the first polyanionic polymer comprises polymer strands formed from at least one ethylenically unsaturated monomer, wherein the polymer strands are linked by at least one linking moiety comprising a hydrolytically susceptible bond.

12. The method of claim 11, wherein at least one of which monomers has:
   i) one or more functional groups that can be titrated with base to form negatively charged functional groups, or
   ii) one or more precursor groups that are precursors of the functional groups that can be titrated with base; which precursor groups are converted to the functional groups; wherein at least one of the following conditions applies:
   a) the first polyanionic polymer is crosslinked with an ethylenically unsaturated crosslinking agent and the mole fraction of ethylenic double bonds in the combination from which the polyanionic polymer is made that is contributed by the ethylenically unsaturated crosslinking agent is 0.02 or less; or
   b) the ratio of macroviscosity of the microgel to the microviscosity of the microgel is 10,000 or less.

13. A method for reducing or inhibiting formation or reformation of adhesions comprising the step of administering to an area affected by a trauma susceptible to giving rise to adhesions an effective amount of a composition comprising a hydrolytically susceptible polyanionic polymer which is a microgel and comprises polymer strands formed from at least one ethylenically unsaturated monomer, wherein the polymer strands are linked by at least one linking moiety comprising a hydrolytically susceptible bond.

14. A method of inhibiting or reducing the formation of adhesions following implantation of an implantable device comprising treating a surgical implant with a composition comprising a hydrolytically susceptible polyanionic polymer which is a microgel and comprises polymer strands formed from at least one ethylenically unsaturated monomer, wherein the polymer strands are linked by at least one linking moiety comprising a hydrolytically susceptible bond.

* * * * *